(12) United States Patent
Wihl et al.

(10) Patent No.: US 7,126,699 B1
(45) Date of Patent: Oct. 24, 2006

(54) SYSTEMS AND METHODS FOR MULTI-DIMENSIONAL METROLOGY AND/OR INSPECTION OF A SPECIMEN

(75) Inventors: Tim Wihl, Fremont, CA (US); Stephen Hiebert, Milpitas, CA (US); Frank Kole, San Jose, CA (US); Richard Schmidley, San Jose, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 448 days.

(21) Appl. No.: 10/688,503

(22) Filed: Oct. 17, 2003

Related U.S. Application Data

(60) Provisional application No. 60/419,793, filed on Oct. 18, 2002.

(51) Int. Cl.
*G01B 11/02* (2006.01)
(52) U.S. Cl. .................. 356/625; 356/602; 356/631
(58) Field of Classification Search ........ 356/601–602, 356/625, 627, 630–631, 237.2, 237.5
See application file for complete search history.

(56) References Cited

U.S. PATENT DOCUMENTS

| | | | | |
|---|---|---|---|---|
| 4,063,820 A | * | 12/1977 | Borgese | .................. 356/625 |
| 5,999,266 A | * | 12/1999 | Takahashi et al. | ....... 356/237.5 |
| 6,181,472 B1 | | 1/2001 | Liu | |
| 6,268,923 B1 | | 7/2001 | Michniewicz et al. | |
| 6,603,103 B1 | * | 8/2003 | Ulrich et al. | ............... 356/601 |
| 2002/0018118 A1 | | 2/2002 | Coulombe et al. | |

FOREIGN PATENT DOCUMENTS

| | | |
|---|---|---|
| WO | 00/36525 | 6/2000 |
| WO | 01/71279 | 9/2001 |

\* cited by examiner

*Primary Examiner*—Richard A. Rosenberger
(74) *Attorney, Agent, or Firm*—Ann Marie Mewherter; Daffer McDaniel, LLP

(57) ABSTRACT

Systems and methods for multi-dimensional metrology and inspection of a specimen such as a bumped wafer are provided. One method includes scanning the specimen with partial oblique illumination to form an image of the structure, either through the normal collection angle or through an oblique collection angle. The method also includes integrating an intensity of the image and determining a height of the structure from the integrated intensity. The integrated intensity may be approximately proportional or inversely proportional to the height of the structure. In addition, the method may include scanning the specimen with bright field illumination to form a bright field image of the specimen. The method may also include determining a lateral dimension of the structure from the bright field image. Furthermore, the method may include detecting defects on the specimen from the bright field image or the obliquely-illuminated image.

42 Claims, 19 Drawing Sheets

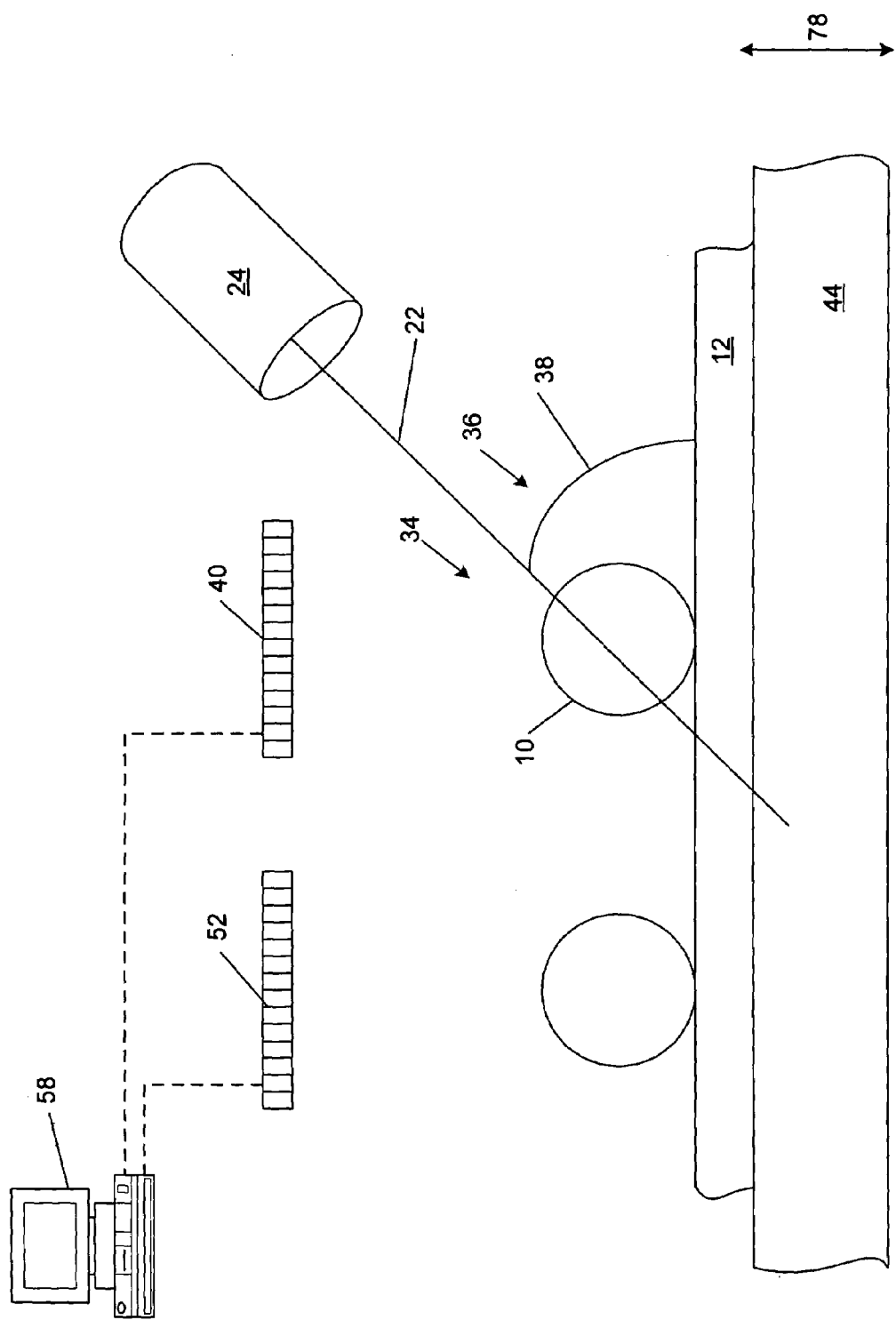

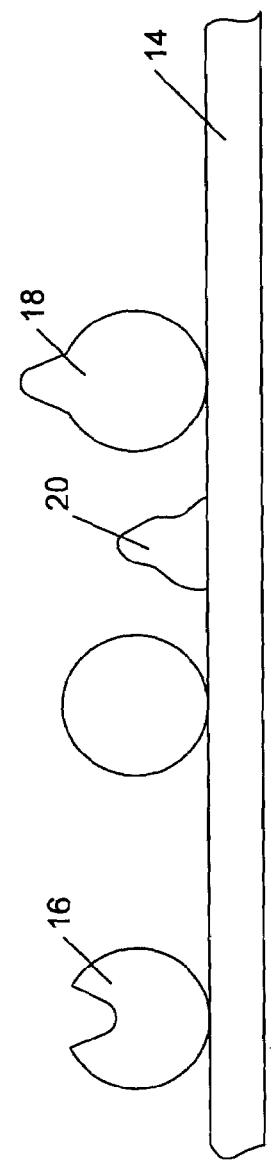
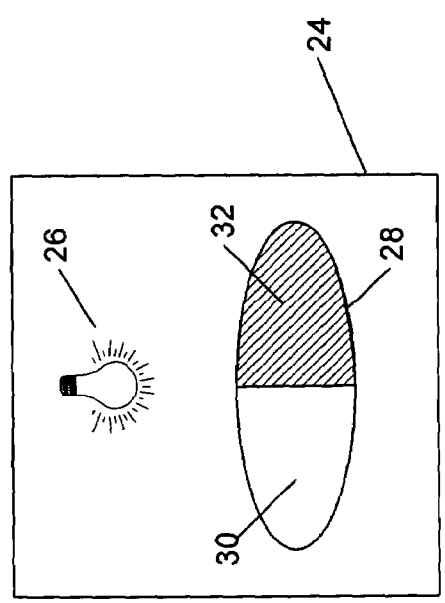

US 7,126,699 B1

SYSTEMS AND METHODS FOR MULTI-DIMENSIONAL METROLOGY AND/OR INSPECTION OF A SPECIMEN

PRIORITY CLAIM

This application claims priority to U.S. Provisional Application No. 60/419,793 entitled "Systems and Methods for Multi-Dimensional Metrology and/or Inspection of a Specimen," filed Oct. 18, 2002.

BACKGROUND OF THE INVENTION

1. Field of the Invention

The present invention generally relates to systems and methods for three-dimensional metrology and/or inspection of a specimen. Certain embodiments relate to systems and methods for metrology and inspection of a specimen such as a bumped wafer.

2. Description of the Relevant Art

Fabricating semiconductor devices such as logic and memory devices typically includes processing a specimen such as a wafer using a number of semiconductor fabrication processes to form various features and multiple levels of the semiconductor devices. For example, lithography is a semiconductor fabrication process that typically involves transferring a pattern to a resist arranged on a wafer. Additional examples of semiconductor fabrication processes may include, but are not limited to, chemical-mechanical polishing, etch, deposition, ion implantation, and electro-chemical plating. Multiple semiconductor devices may be fabricated in an arrangement on a wafer and then separated into individual semiconductor devices.

Prior to being separated into individual semiconductor devices, an entire wafer of semiconductor devices may be prepared for packaging. Packaging may include coupling a chip carrier such as a substrate to a semiconductor device. A chip carrier may provide mechanical strength, heat transfer, and environmental protection to a semiconductor device. In addition, a chip carrier may include electrical wiring or other electrical structures such that electrical connection may be made between a semiconductor device and another structure such as a card-on-board ("COB") structure for a computer system. Preparing a wafer of semiconductor devices for packaging may include forming structures on a surface of the semiconductor devices that may be used to couple a semiconductor device to a chip carrier. For example, relatively small solder balls may be arranged in an area on a semiconductor device. Such relatively small solder balls may be commonly referred to as "bumps," and a wafer on which such solder balls are formed may be commonly referred to as a "bumped wafer." The solder balls may be configured to physically attach the semiconductor device to a chip carrier and to make electrical connection to a chip carrier. For example, a device may be placed on a substrate, and the solder balls may contact and melt onto an array of metal pads on the substrate. Such a packaging method may be commonly referred to as face-down bonding, flip-chip bonding, or controlled collapse chip connections ("C4").

Bumps that are incorrectly formed on a wafer may cause significant problems during further processing such as probing of the wafer and during use of the device. For example, incorrectly formed bumps may damage probes on a probe card thereby causing tester downtime and incurring tester repair costs. Incorrectly formed bumps may also bridge power and ground contacts thereby resulting in excessive current draw through a probe card. Therefore, bumped wafers may typically be inspected and measured prior to probing. In addition, incorrectly formed bumps may not be detected during probing and may increase the potential for failure of a packaged device. Furthermore, probing may damage bumps especially on a wafer having a relatively high number of bumps per unit area that may require high vertical forces during testing to seat probes for proper contact. In this manner, inspection and metrology of a bumped wafer may also be performed after wafer probing.

Currently available methods for three-dimensional inspection, which may be commonly referred to as "defect detection," and metrology of bumped wafers generally include first acquiring data in the x-y plane and then acquiring data in the z plane. Essentially, such systems may be described as being serial in data acquisition (i.e., two-dimensional ("2D") data acquisition followed by three-dimensional ("3D") data acquisition). For bumped wafers, 2D defects may include, for example, missing bumps, improperly located bumps, bridged bumps, large-diameter bumps, and small-diameter bumps. Examples of 3D defects may include, but are not limited to, bumps that may be too tall or too short or that may have protruding vertical spikes or recessed vertical pits. Because currently available methods are generally not capable of simultaneous 2D and 3D data acquisition, such methods may be significantly slower than either 2D or 3D data acquisition. In addition, 3D data acquisition may be significantly slower than 2D data acquisition thereby resulting in substantially reduced sampling for 3D in comparison to sampling for 2D. As used herein, the term "sampling" generally refers to the number of points or locations inspected or measured on a single specimen during a process. In other words, if a relatively large percentage of a wafer may be scanned to acquire x-y data, then only a much smaller percentage of the wafer may be scanned to acquire additional z data.

One currently available system, the ABI-2000 automatic bump inspection system, available from KLA-Tencor, San Jose, Calif., is configured to scan a wafer using bright field, white light imaging with image data captured using a charge coupled device ("CCD") camera and a frame-grabber. A frame-grabber is a device that may be configured to receive a signal from a detector such as a CCD camera and to convert the signal (i.e., to digitize an image). In such a system, inspection and metrology algorithms are used to detect defects in the x-y plane and to make measurements in the x and y directions. Such a system is also configured to re-scan, or "revisit," select locations on the wafer to acquire 3D data for individual bumps. This revisiting uses laser scanning microscopy and incremental z movement of the wafer along with additional algorithms to detect bump defects in the z plane and to make bump measurement in the z-direction.

In another example, systems developed and manufactured by Robotic Vision Systems, Inc., Canton, Massachusetts, e.g., Model Nos. WS-1000 and WS-2000, incorporate 2D vision technology using a time delay integration ("TDI") camera and low-angle ring light or co-axial light. Such systems are configured to first scan a wafer to detect typical 2D bump defects and surface defects. Such systems are also configured to perform a second wafer scan using a laser triangulation technique to acquire 3D metrology measurements and to detect 3D bump defects. An example of a laser triangulation technique is illustrated in U.S. Pat. No. 6,181,472 to Liu, and is incorporated by reference as if fully set forth herein.

In yet another example, systems developed and manufactured by August Technology Corporation, Bloomington, Minn., e.g., the NSX bump inspection system, incorporate 2D vision technology using a high-resolution CCD camera and strobe illumination. Such systems are configured to first inspect a wafer to acquire 2D data for 2D defect detection of bumps and defect detection elsewhere on the surface of the wafer. For 3D data acquisition, relatively small, select regions of the wafer are revisited. At each of the smaller regions, the system may use automatic focusing at different vertical locations to determine the height of all bumps in the field of view.

Another example of a system for measuring 3D surface topography provides high resolution contour measurements of an object using interferometric methods. The system includes an optical head that is a moiré-type interferometer optical head employing co-sight detector phase shifting. Ronchi gratings are placed at image planes to produce moiré fringe patterns indicating the contour of the surface. The moiré images are relayed to detector planes, and CCD camera arrays view exactly the same image of the part except for the fringe pattern superimposed on the image. The images, and bucket images collected from a known reference surface needed to properly compensate the images and phase data, are used with a standard bucket phase algorithm. Output of the algorithm is analogous to the surface contour of the sample inspected. One example of such a system is illustrated in U.S. Pat. No. 6,268,923 B1 to Michniewicz et al., which is incorporated by reference as if fully set forth herein.

An additional example of a moiré-type system for 3D inspection of an object includes a source of light projected through a grid assembly. An image acquisition apparatus includes one or more cameras with an array of pixels in the form of a CCD camera. The system is used to simultaneously project at least three phase-shifted grids onto an object, to simultaneously take an image of each of the phase-shifted grids on the object, to gather an intensity value for each pixel of the images, and to compute the phase for each pixel of the image using the intensity images. The above steps are performed for a reference object and the object to be measured. The difference of height between the object and the reference object for every pixel is computed by using the respective phases for each pixel, and the relief of the object for each pixel is determined using the difference of height at every pixel. An example of such a system is illustrated in U.S. Patent Application Publication No. US 2002/0018118 A1 to Coulombe et al. and PCT International Publication No. WO 01/71279 A1 to Coulombe et al., which are incorporated by reference as if fully set forth herein.

There are several disadvantages to the moiré-type systems and methods for three-dimensional inspection of objects. For example, these systems and methods include complex system configurations and rely on data collected from a separate reference object. Therefore, the methods have a lower throughput than methods that do not require a separate reference. In addition, the systems measure and use a sine wave pattern to determine the surface contour or relief of the object. Therefore, the sensitivity of the system may vary for objects of different heights. For example, the system may be more sensitive to measurements that correspond to a slope of the sine wave pattern than to measurements that correspond to a crest or valley of the sine wave pattern. In addition, using such a sine wave pattern may yield inaccurate height measurements. For example, the period of the sine wave pattern may be selected to correspond to a range of expected heights. However, if the height of an object is outside of this range, the height of the object may be inaccurately reported with an error of one or more times the range of heights.

There are several additional disadvantages to currently available systems and methods for three-dimensional inspection of bumped wafers. For example, as described above, such systems are configured to scan a wafer more than once in series to acquire 2D and 3D data for inspection and metrology. In addition, configurations of such systems are incompatible with rapid scanning of relatively large areas of bumped wafers. Such disadvantages will generally lower a throughput of an inspection and metrology system. Furthermore, such systems may be relatively complex due to the use of separate 2D and 3D data acquisition and processing systems. This disadvantage will generally increase cost and reduce reliability of an inspection and metrology system.

SUMMARY OF THE INVENTION

Systems and methods capable of performing high speed, multi-dimensional metrology and inspection of a specimen are provided. An embodiment relates to a system configured to determine a dimension of a structure on a specimen. In an embodiment, the structure may include, but is not limited to, a bump, a ball, or a surface of the specimen. In addition, the specimen may include, but is not limited to, a wafer, a sawn die, or an integrated circuit package. In another embodiment, the structure may include a three-dimensional defect.

The system includes a partial oblique illumination system configured to project a knife edge terminator on the specimen. In one embodiment, the partial oblique illumination system includes an objective lens configured to image the knife edge terminator on the specimen. The objective lens may have a numerical aperture selected such that an angle at which the knife edge terminator is projected onto the specimen is substantially constant.

The system also includes an imaging system configured to image the structure as the structure passes across the knife edge terminator and to integrate an intensity of the images of the structure. In an embodiment, the imaging system includes a time delay integration (TDI) sensor configured to image the structure and to integrate the intensity. In some embodiments, the TDI sensor may be operated at a speed greater than a speed of a stage on which the specimen is supported during imaging such that the images are smeared. In another embodiment, the TDI sensor may have an asymmetrical pixel size such that pixels of the sensor have a dimension in a scan direction that is smaller than a dimension of the pixels in a direction opposite to the scan direction. In yet another embodiment, anamorphic optics may be coupled to the TDI sensor such that the image is magnified in a scan direction.

In one embodiment, the imaging system may also be configured to image the structure as the structure passes across an additional knife edge terminator projected onto the specimen at an azimuthal angle different than an azimuthal angle at which the knife edge terminator is projected on the specimen. In one such embodiment, the imaging system may include a measurement TDI sensor configured to image the structure as it passes across the knife edge terminator and a reference TDI sensor configured to image the structure as it passes across the additional knife edge terminator. In some embodiments, the additional knife edge terminator may be inverted with respect to the knife edge terminator.

In different embodiments, the partial oblique illumination system may be configured to project two or more knife edge terminators on the specimen at the same azimuthal angle. In one such embodiment, the imaging system may include a measurement TDI sensor configured to image the structure as it passes across a first of the two or more knife edge terminators. The imaging system may also include a reference TDI sensor configured to image the structure as it passes across a second of the two or more knife edge terminators. In a different embodiment, the imaging system may include a measurement TDI sensor configured to form multiple, separate images of the structure as it passes across each of the two or more knife edge terminators. In some embodiments, an additional TDI sensor or sensors may be placed at non-normal angles.

In addition, the system includes a processor coupled to the imaging system. The processor is configured to determine a height of the structure from the integrated intensity. The integrated intensity may be proportional or inversely proportional to the height of the structure. In some embodiments, the processor may also be configured to determine a height of the specimen from the integrated intensity.

In another embodiment, the imaging system may be configured to form a reference image of the structure in full oblique illumination and to integrate an intensity of the reference image. In one such embodiment, the processor may be configured to reduce albedo differences between the structure and additional structures on the specimen using the reference image. In another such embodiment, the processor may be configured to determine the height of the structure from the integrated intensities of the image and the reference image.

In some embodiments, the system may also include a stage configured to support the specimen during imaging. A vertical position of the stage is substantially constant during imaging. The system may be further configured as described herein.

An additional embodiment relates to a method for determining a dimension of a structure on a specimen. The structure and the specimen may include any of those described herein. The method includes scanning the specimen with partial oblique illumination to form an image of the structure. In one embodiment, scanning may include imaging the structure as it passes across an obliquely-projected knife edge terminator on the specimen. In some embodiments, an angle of the partial oblique illumination may be substantially constant during scanning.

In another embodiment, the method may include scanning the specimen with additional partial oblique illumination at an azimuthal angle different than the partial oblique illumination to form an additional image of the structure and integrating an intensity of the additional image. In an alternative embodiment, scanning the specimen may include projecting two or more knife edge terminators on the specimen at the same azimuthal angle. In one such embodiment, scanning may further include forming multiple exposures of the structure as it passes across each of the two or more knife edge terminators. In some embodiments, the image may be a smeared image of the structure. In a different embodiment, the image may be magnified in a direction in which scanning is performed.

The method also includes integrating an intensity of the image. In addition, the method includes determining a height of the structure from the integrated intensity. The integrated intensity is proportional or inversely proportional to the height of the structure. In some embodiments, the method may also include determining a height of a surface of the specimen from the integrated intensity.

In one embodiment, the method may also include scanning the specimen with full oblique illumination to form a reference image of the structure, integrating an intensity of the reference image, and reducing albedo differences between the structure and additional structures on the specimen using the reference image. In another embodiment, determining the height of the structure may include determining the height of the structure from the integrated intensities of the image and the reference image.

In yet another embodiment, the method may include maintaining a substantially constant vertical position of the specimen during scanning. The method may further include any other steps of any other method described herein.

Another embodiment relates to a system configured to determine a dimension of a structure on a specimen. The system includes a first imaging system configured to form an image of the structure by scanning the specimen with partial oblique illumination. The system also includes a second imaging system configured to form a bright field image of the specimen by scanning the specimen with bright field illumination. In one embodiment, the first and second imaging systems are configured to scan the specimen in the same pass. In addition, the system includes a processor coupled to the first and second imaging systems. The processor or the first imaging system is configured to integrate an intensity of the image. The processor is also configured to determine a height of the structure from the integrated intensity, to detect defects on the specimen from the bright field image, and to determine a lateral dimension of the structure from the bright field image. This system may be further configured as described herein.

A further embodiment relates to a method for determining a dimension of a structure on a specimen. The method includes scanning the specimen with partial oblique illumination to form an image of the structure. The method also includes integrating an intensity of the image. In addition, the method includes scanning the specimen with bright field illumination to form a bright field image of the specimen. In some embodiments, scanning the specimen with partial oblique illumination and scanning the specimen with bright field illumination are performed substantially simultaneously. The method further includes detecting defects on the specimen from the image or the bright field image. Furthermore, the method includes determining a height of the structure from the integrated intensity and a lateral dimension of the structure from the bright field image. The method may include any other steps of any methods described herein.

One advantage of the systems and methods described herein is that high speed scanning for both two-dimensional and three-dimensional data acquisition are provided. An additional advantage is that two-dimensional and three-dimensional defect detection and metrology may be performed in a single pass. A further advantage is that independent techniques and hardware systems are not required to accomplish the two-dimensional and three-dimensional data acquisitions. Furthermore, if common hardware systems are used to perform multiple tasks, then the system may include fewer components and may have more relaxed design tolerances. For example, the system may include fewer mechanical and electrical components. In addition, the systems and methods as described herein may be more sensitive, and particularly more sensitive over a relatively large field of view, than currently available systems and methods for three-dimensional data acquisition.

BRIEF DESCRIPTION OF THE DRAWINGS

Further advantages of the present invention may become apparent to those skilled in the art with the benefit of the following detailed description of the preferred embodiments and upon reference to the accompanying drawings in which:

FIG. 1 is a partial schematic cross-sectional view of an embodiment of a system configured to determine a dimension of a structure on a specimen;

FIG. 2 is a partial schematic cross-sectional view of examples of various three-dimensional defects formed on a specimen;

FIG. 3 is a partial schematic cross-sectional view of an embodiment of an illumination system;

Figure 4:
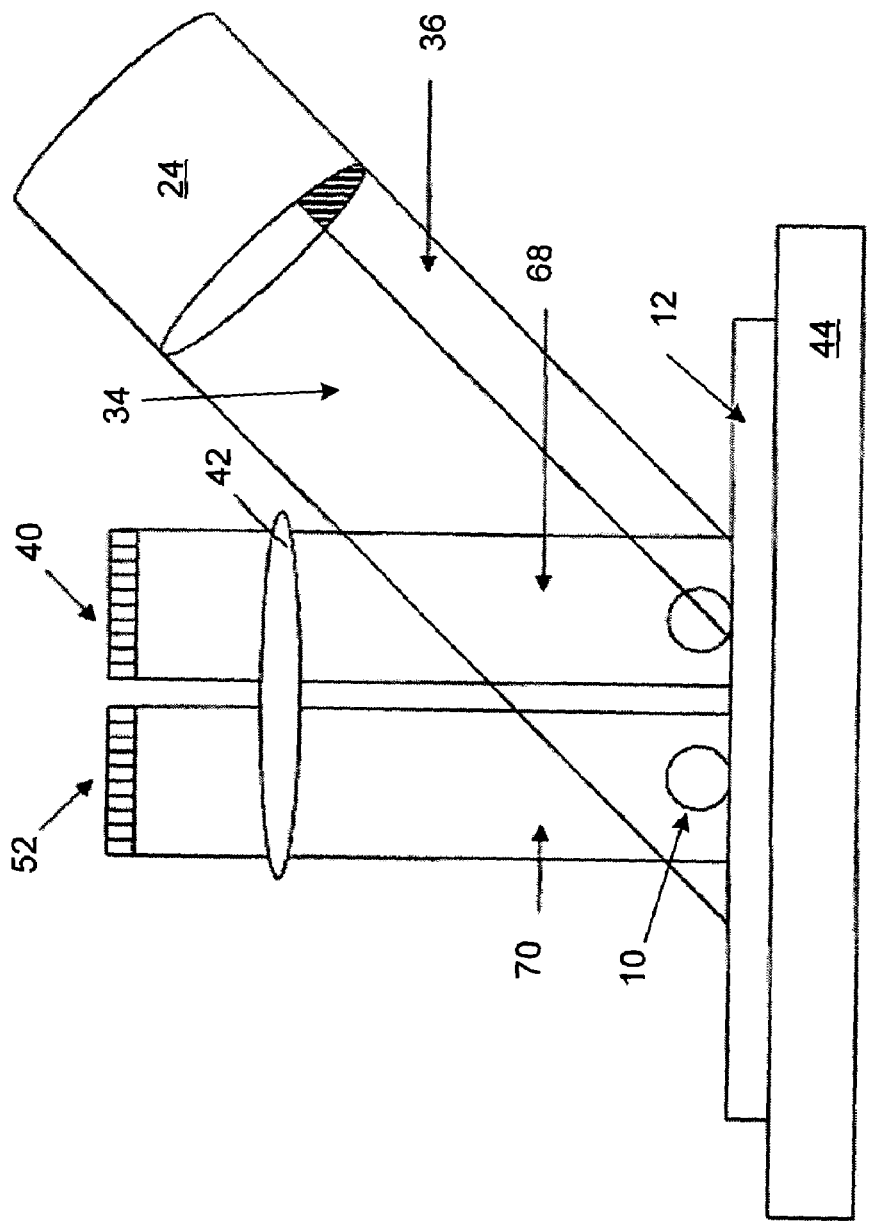
FIG. 4 is a partial schematic cross-sectional view of an embodiment of an optical system configured to measure a dimension of a structure on a specimen.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

The following description generally relates to systems and methods for determining a dimension of a structure on a specimen. Various embodiments relate to a system that may include an imaging system configured to relate structure heights directly to image exposure duration, a processor configured to determine a height of a structure from exposure differences, and an imaging system coupled to a processor that provides lateral (two-dimensional) metrology and defect detection. Such a system may be configured to perform inspection and metrology in three-dimensions within the same pass.

As will be further described herein, elements that may be similarly configured in each of the embodiments illustrated in FIGS. 1–19 have been indicated by the same reference characters. It is noted that FIGS. 1–19 are not drawn to scale. In particular, the scale of some of the elements of the figures is greatly exaggerated to emphasize characteristics of the elements. It is also noted that FIGS. 1–19 are not drawn to the same scale.

FIG. 1 illustrates a partial schematic side view of an embodiment of a system configured to determine a dimension of structure 10 on specimen 12. Structure 10 may include, but is not limited to, a bump. As described herein, a bump may be a relatively small solder ball that may be used to couple a semiconductor device to a chip carrier. The structure, however, may also include gold bumps, solder paste bumps, or any other bumps known in the art. In addition, the bumps may include reflowed bumps or "as-deposited" (plated, printed, sputtered, or evaporated) bumps. Specimen 12 may be a wafer. A wafer may include a monocrystalline silicon substrate suitable for the fabrication of integrated circuits. In this manner, specimen 12 may be commonly referred to as a "bumped wafer." The specimen may also include a wafer produced by wafer-level packaging processes such as, but not limited to, UltraCSP available from Kulicke & Soffa Flip Chip Division, Phoenix, Ariz., wCSP available from Integrated Electronics and Packaging Technologies, Inc. (Casio/Oki), Hachioji, Japan, and Super CSP available from Fujitsu Microelectronics America, Inc., San Jose, Calif. In addition, the specimen may include a post-saw bump or wafer-level packaging wafer on film and in film frame. Furthermore, the specimen may include individual bumped die or integrated circuit packages in die/package carriers.

The specimen, however, may also include a ball grid array (BGA) type package on a package carrier. The specimen may further include a thin-film head die formed on a wafer or as an individual die after saw. Furthermore, the specimen may include a micro-electro-mechanical system (MEMS) device processed on a wafer. In addition, the specimen may include, but is not limited to, photonics and optoelectronic devices such as lasers, waveguides and other passive components processed on wafers, print heads, and bio-chip devices processed on wafers.

The specimen may also include any specimen known in the art that includes a structure having a dimension of interest in a plane substantially perpendicular to a plane of an upper surface of the specimen. In addition, the height of the upper surface of the specimen may be of interest as well. For example, the specimen may include any specimen that has one or more three-dimensional (3D) defects formed thereon. A 3D defect, as used herein, refers to any abnormal structure formed on a specimen having a dimension of interest in a direction substantially perpendicular to an upper surface of the specimen. FIG. 2 illustrates a partial schematic cross-sectional view of examples of various 3D defects formed on specimen 14. As shown in FIG. 2, one example of a 3D defect is bump 16 having a recessed vertical pit. Another example of a 3D defect is bump 18 having a protruding vertical spike. An additional example of a 3D defect is unwanted material 20 formed on the specimen.

The system may include an imaging system configured to form an image of the structure by scanning specimen 12 with partial oblique illumination 22, as shown in FIG. 1. For example, the imaging system may include illumination system 24 configured to project partial oblique illumination 22 onto specimen 12. FIG. 3 illustrates a partial schematic side view of an embodiment of illumination system 24. As shown in FIG. 3, illumination system 24 includes light source 26. Light source 26 may be configured to emit broadband light. For example, light source 26 may include, but is not limited to, a white light source. Alternatively, light source 26 may be configured to emit monochromatic or narrow band light. For example, light source 26 may include, but is not limited to, a laser or a light emitting diode (LED) configured to emit light having a single wavelength or a narrow band of wavelengths of light. The single wavelength or narrow band of wavelengths of light may include, for example, blue light, green light, or red light. The wavelength of the light source such as a laser or an LED may vary depending upon, for example, characteristics of structures 10 and/or specimen 12. For example, if the specimen includes a resist layer, an appropriate wavelength of light may include green light. Alternatively, if the specimen includes a material such as copper or gold, an appropriate wavelength of light may include red light. In addition, light source 26 may be configured to emit light other than visible light such as ultraviolet light and infrared light.

The illumination system may also include multiple light sources, a wavelength selection device such as one or more filters coupled to a broadband light source, or another light source or device known in the art such that a wavelength of partial oblique illumination 22 may vary depending upon a structure and/or a specimen being inspected or measured. For example, a controller coupled to the illumination system may be configured to alter a parameter of the light source or a filter, and thereby a wavelength of light, of the illumination system depending upon instructions provided from a processor. The instructions may vary depending on indication of characteristics of a structure and/or specimen included in a program recipe being run on the system.

As further shown in FIG. 3, illumination system 24 may include objective lens 28. Objective lens 28 may be configured to image a knife edge terminator onto the specimen. For example, light may pass through portion 30 of objective lens 28, but not portion 32 of objective lens 28. Portions 30 and 32 may be separated by a single sharp line. The objective lens may be configured such that the knife edge terminator may be located at a focal point at approximately the back focal position of the objective lens. In this manner, the illumination system may be configured to image a single sharp line onto the specimen separating illuminated areas 34 on the specimen from substantially non-illuminated areas 36 on the specimen across a field of view of the imaging system, as shown in FIG. 1. The image of the knife edge terminator on the specimen may have a length approximately equal to, or greater than, the field of view of the system. The objective lens may also be equivalent to an acquisition objective (not shown) configured to collect light returned from the specimen. Objective lens 28 may also be configured to collimate light from light source 26. In addition, the illumination system may include any optical element configurable to image a single sharp terminator over the field of view of the imaging system instead of objective lens 28. Furthermore, the illumination system may include gratings, slits, or other optical elements configured to produce a gradient of alternating light and dark areas on the specimen instead of a single sharp terminator. In this manner, the imaging system may or may not be configured to image a single sharp terminator on the specimen across the field of view of the imaging system. Some examples of such imaging systems are described further below.

The objective lens may also have a numerical aperture selected such that an angle of the partial oblique illumination may be substantially constant. For example, the objective lens may have a relatively low numerical aperture. In this manner, the illumination system may have a substantially constant angle of illumination across the field of view. Angle of illumination 38, as shown in FIG. 1, may be in a range from approximately 30° to approximately 75°. For example, the angle of illumination may be approximately 45°. The angle of illumination may vary, however, depending upon, for example, an average height or a range of heights of structures on the specimen. For example, as the angle of illumination decreases, resolution of, or sensitivity to, height of structures on the specimen increases, and sensitivity to an aspect ratio of the structures increases. The angle of illumination may also vary depending on the type of structure formed on the specimen. For example, if the structures are trenches, then a relatively high angle of illumination may be appropriate.

Furthermore, the imaging system may be configured such that the angle of illumination may be altered depending upon the structures and/or the specimen being inspected or measured. For example, a controller coupled to the illumination system may be configured to alter a position, and thereby an angle of illumination, of the illumination system depending upon instructions provided from a processor. The instructions may vary depending on indication of a structure and/or specimen type included in a program recipe being run on the system.

The imaging system may also include time delay integration (TDI) sensor 40, which may also be referred to herein as a "measurement TDI." TDI sensor 40 may be coupled to an optical system (not shown) configured to focus light returned from the specimen onto the TDI sensor. A simplified representation of such an optical system is illustrated in FIG. 4. As shown in FIG. 4, optical system 42 focuses light returned from specimen 12 onto TDI sensor 40. The optical system may include an acquisition lens equivalent to the objective lens described above. The acquisition lens may also be configured to have a variable magnification depending on, for example, ranges of height of structures and/or specimens, being inspected and/or measured, and selected resolving capability. The acquisition lens may include any collection lens or objective lens known in the art.

TDI sensor 40 may be configured to detect the partial oblique illumination returned from the specimen. The TDI sensor may have a length approximately equal to, or less than, a length of the knife edge terminator imaged on the specimen by the partial oblique illumination. The TDI sensor may include a plurality of pixels arranged in the direction that a specimen is scanned. The pixels may be clocked by the TDI sensor as the specimen is passed across the field of view. As the structures are passed across the oblique plane formed by the partial oblique illumination, the structures will be illuminated depending upon their heights and upon the configuration of the illuminated and non-illuminated regions. For example, if the illuminated region is configured to be above the non-illuminated region (the volume above the terminator line receives light from the oblique source), the taller structures will receive more total illumination and will return more total light than shorter structures.

In this manner, the images formed by the sensor will vary depending upon a height of the structures and are a measurement of how much time the structures spend in illuminated volume 34 of partial oblique illumination 22. For the case in which the illuminated volume is located above the terminator, the time that structures spend in illuminated areas 34 of partial oblique illumination 22 may be approximately proportional to a height of the structures. TDI sensor 40 may also be configured to integrate an intensity of the image formed by scanning the specimen with partial oblique illumination 22. Therefore, the total integrated brightness of images of the structures may be approximately proportional to a height of the structures. Conversely, if the illuminated volume is located below the terminator, the integrated brightness of the images of the structures may be approximately inversely proportional to the heights of the structures. Hereafter, all discussions of this measurement effect apply to both configurations of the illuminated and non-illuminated regions, even if only one may be mentioned as an example.

Figure 5:
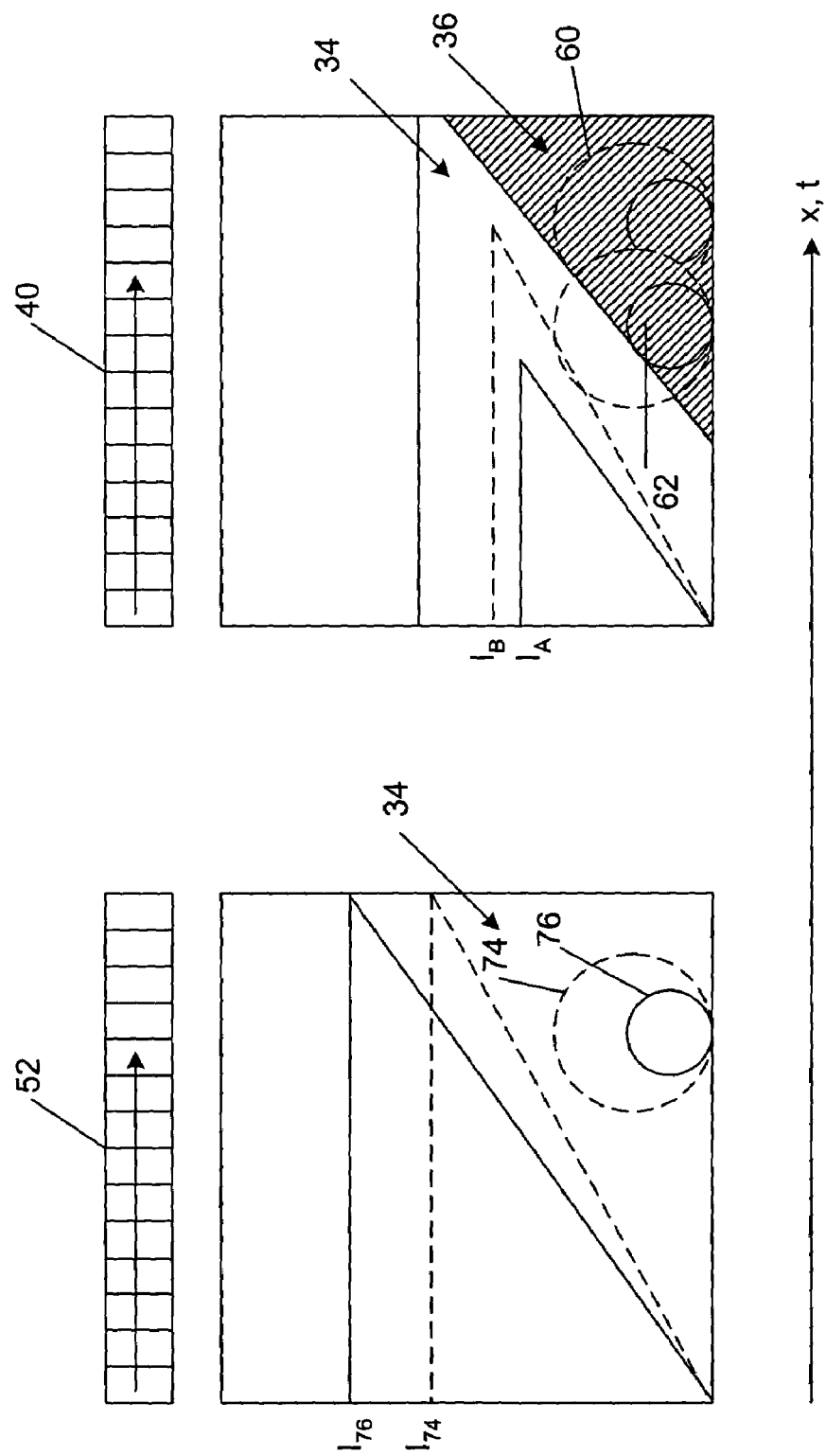
FIG. 5 is a schematic diagram of intensities of various structures illuminated with partial oblique illumination and full oblique illumination.

As shown in FIG. 5, the specimen is scanned in direction x over a period of time, t. In other embodiments, the specimen may be scanned in other directions such as a y-direction, which is substantially perpendicular to the x-direction, over a period of time, t. The partial oblique illumination may be arranged at an azimuthal angle with respect to the scanning direction. For example, the partial oblique illumination may be arranged at an azimuthal angle of about 0° or about 90° with respect to the scanning direction. Bumps 60 having a height greater than bumps 62 will spend a longer period of time in illuminated area 34 of the partial oblique illumination. TDI sensor 40 forms an image of bumps 60 and 62 as the images move across the TDI sensor. Therefore, intensity $I_B$ and $I_A$ of the images of bumps 60 and 62, respectively, integrated over time by the TDI sensor will be approximately proportional to the height of the structures.

Figure 6:
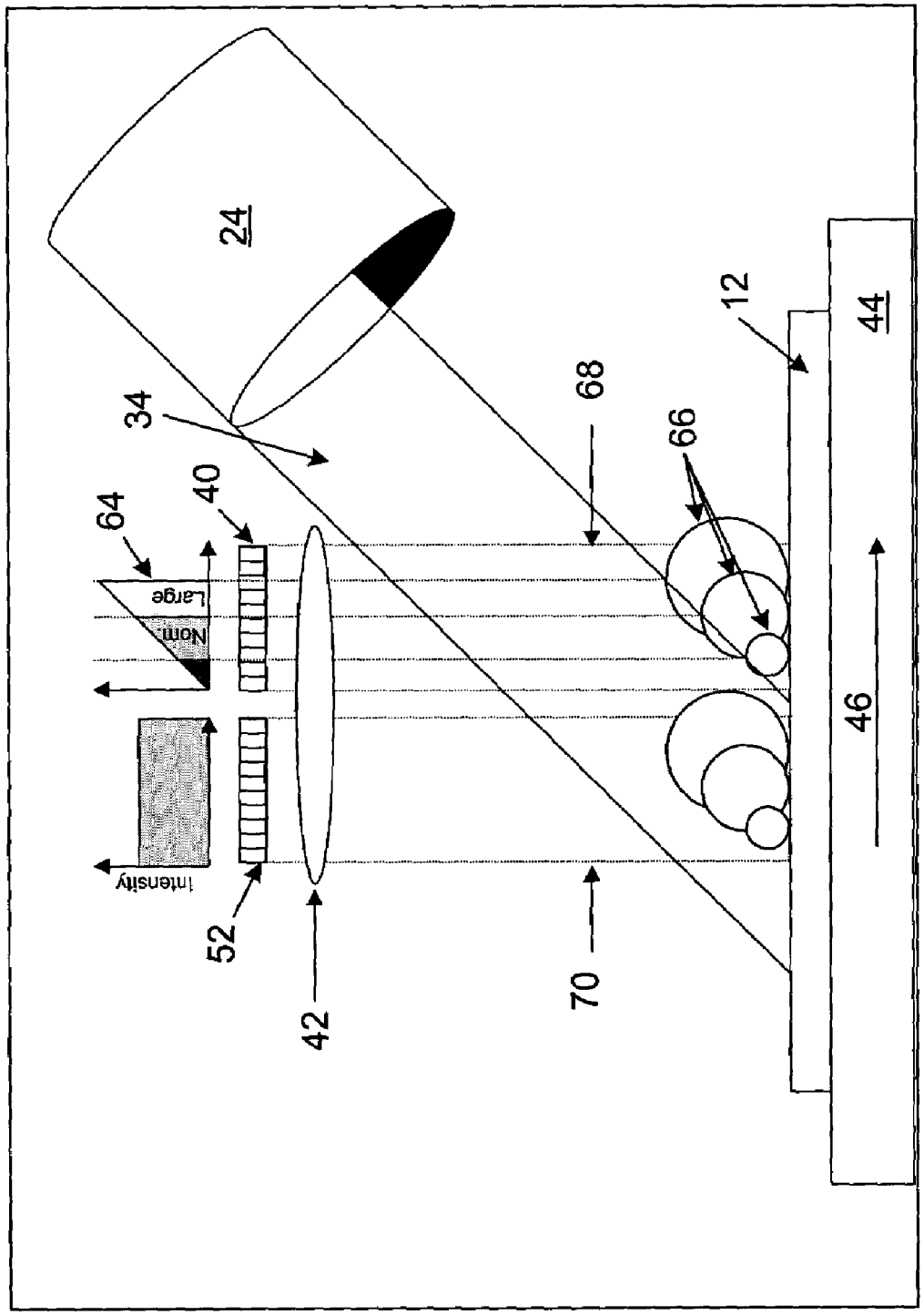
FIG. 6 is a partial schematic cross-sectional view of an embodiment of a system configured to determine a dimension of a structure on a specimen, in which the intensities of images produced by a measurement TDI are proportional to the height of the structure on the specimen.

FIG. 6 illustrates an additional example of how intensity 64 of the images integrated over time by TDI sensor 40 will be approximately proportional to the height of bumps 66 having three different heights. As with other systems described herein, structures are passed across fully-illuminated field of view 70 and partially-illuminated field of view 68. TDI sensors 40 and 52 integrate the images of each structure across multiple stages of their sensors in the same direction as the specimen's motion. The resulting measurement TDI image from TDI sensor 40 has an exposure proportional to the structure's time in the oblique light, which is proportional to its height. The reference TDI 52 provides a fully-illuminated view of the same structure, which may be used to normalize out any reflectance differences between individual structures. The normalized intensity then provides a measure of each structure's height.

Figure 7:
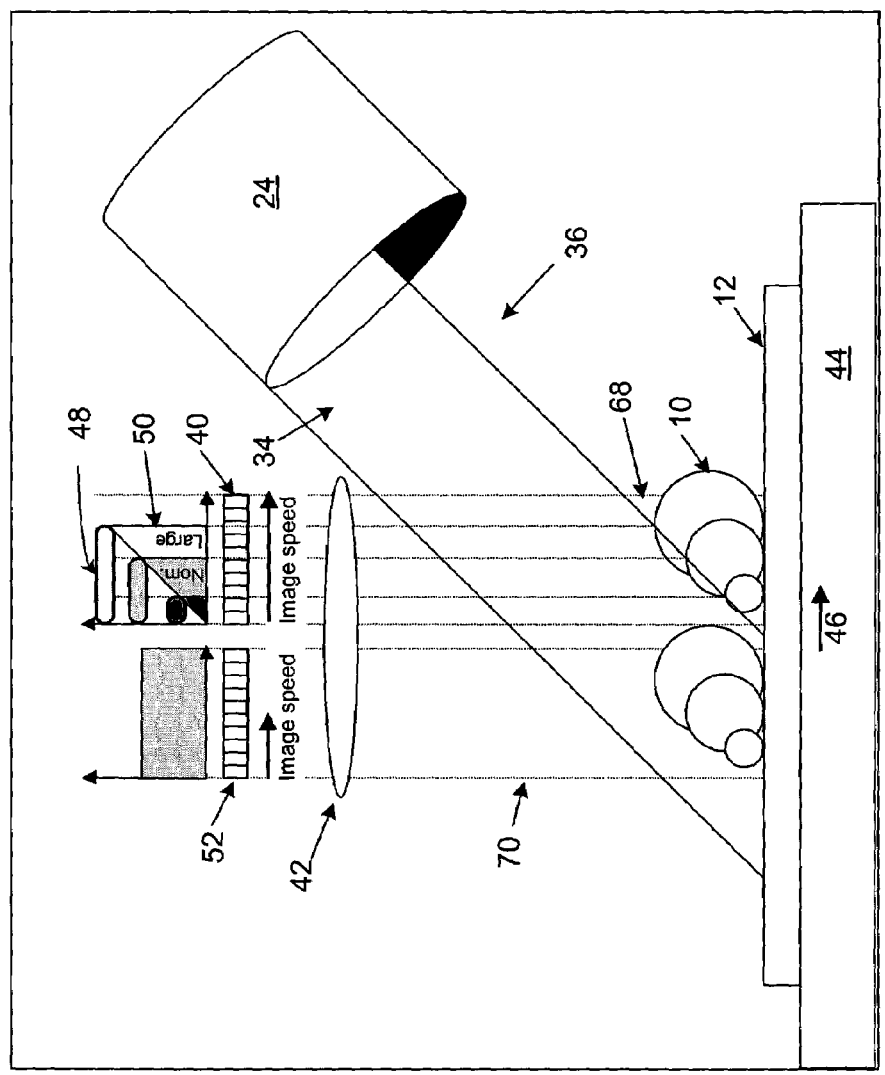
FIGS. 7–8 are partial schematic cross-sectional views of various embodiments of a system configured to determine a dimension of a structure on a specimen that include different measurement TDI configurations.

Another embodiment of system that includes a different configuration of the measurement TDI is illustrated in FIG. 7. In this embodiment, measurement TDI 40 is operated at a speed greater than a speed of stage 44 on which specimen 12 is supported during imaging thereby causing images formed by the measurement TDI to be smeared. Stage 44 is described in more detail below. The stage may be moved in scan direction 46 such that the knife edge terminator is scanned across specimen 12. The knife edge terminator shadow cuts off structure images as they cross from illuminated area 34 to non-illuminated area 36, in proportion to their height. As shown in FIG. 7, the images produced by measurement TDI 40 of structures 10 on specimen 12 have smeared length 48 and intensity 50 that are proportional to their heights.

The over-clocked measurement TDI may be used with a single knife edge terminator but applies a faster clocking frequency to the measurement TDI. The measurement TDI image of the structures will now be "smeared" in the direction of the scan since the sensor will be read out faster than the image is traveling across the sensor. As before, the oblique knife edge terminator cuts off the integration of the structure's image in relation to its height so that the resulting structure's smear length in the measurement image will be proportional to the structure's height. Also, the intensity of each structure's smeared image will be proportional to its height. Reference TDI 52, which is described in more detail below, can operate in the stage-synchronized mode thereby providing intensity normalization or in the over-clocked mode thereby providing both a smear length reference and an intensity normalization.

The above-described configuration improves the signal-to-noise ratio in the measurement image since it spreads the measurement TDI's image across more integration steps. As such, this configuration allows a greater oblique illumination intensity and pushes out the onset of saturation and blooming in the measurement image. This configuration also reduces the shot noise component of the image noise budget. The system shown in FIG. 7 may be further configured as described herein.

Figure 8:
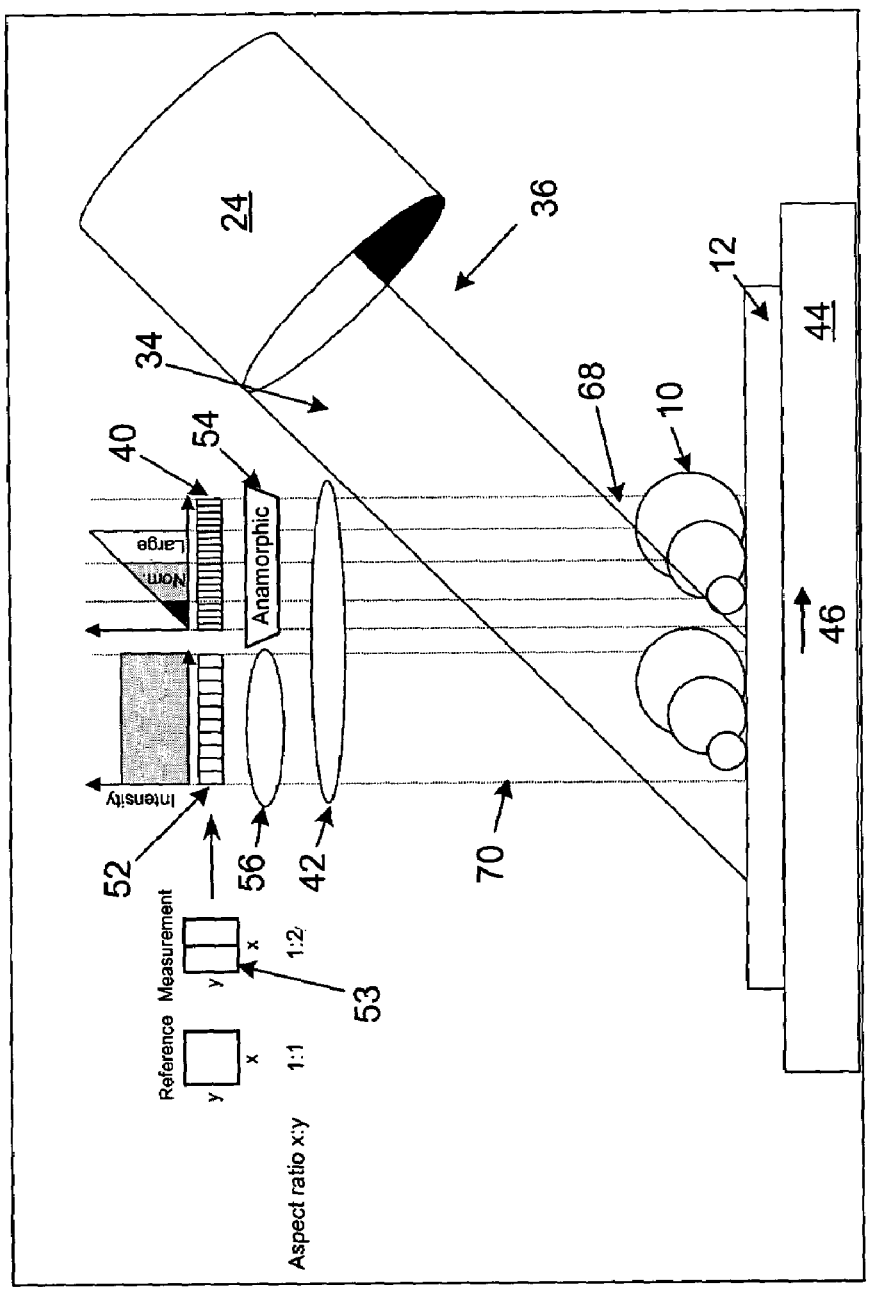

An additional embodiment of a system that includes a different configuration of the measurement TDI is illustrated in FIG. 8. In this embodiment, the effective size of pixels of the measurement TDI are reduced in the x-direction (scan direction 46). This configuration has the effect of magnifying the image in the scan direction only. FIG. 8 illustrates two methods of accomplishing reduction of the pixel size in the x-direction. One method is to alter the physical pixel size of the TDI sensor. In this manner, the measurement TDI may have asymmetrical pixel size 53 such that pixels of the sensor have a dimension in a scan direction that is smaller than a dimension of the pixels in a direction opposite to the scan direction. In one embodiment, the ratio of the pixel size in the x direction to the pixel size in the y direction may be about 1:2. Another method is to position anamorphic optics 54 in front of measurement TDI 40. In this manner, the anamorphic optics are coupled to the sensor such that the image is magnified in scan direction 46. If anamorphic optics 54 are positioned in front of measurement TDI 40, then optical system 56 may be positioned in front of reference TDI 52. Optical system 56 may include an acquisition lens as described herein, or the same or similar anamorphic optics 54, or one or more other suitable optical components.

The measurement TDI with asymmetrical pixel size changes the aspect ratio of the image pixel size (e.g., from 1:1 to 1:2). The pixel width in the direction of the scan (parallel with the TDI clocking direction) is made smaller than the pixel's height in the cross-scan direction (orthogonal to the TDI clocking direction). This change can be accomplished by either coupling anamorphic optics to the measurement TDI or by manufacturing a TDI sensor that has pixel dimensions at this aspect ratio. In either configuration, the aspect ratio change has the effect of magnifying the image in the scan direction thereby compressing the available height measurement range into a shorter integration interval in the scan direction. As such, the imaging system's measurement range may be tuned to improve sensitivity without sacrificing swath height (sensor coverage in the cross-scan direction). In contrast, with a 1:1 pixel aspect ratio, a similar improvement in sensitivity would magnify the image equally in both directions thereby reducing the total height of the sensor coverage and thereby reducing the overall speed of the system to scan specimens. The system shown in FIG. 8 may be further configured as described herein.

The system also includes processor 58 coupled to the imaging system, as shown in FIG. 1. For example, processor 58 is coupled to at least TDI sensor 40. Processor 58 is configured to determine a height of structure 10 and/or the height of the surface of specimen 12 from an integrated intensity generated by TDI sensor 40. Processor 58 may also be configured to integrate the intensity generated by sensor 40 before determining a height of structure 10. The integrated intensity may be approximately proportional to a height of the structure or surface. For example, as described above, images formed by the TDI sensor may indicate how much time the structures spend in illuminated areas of partial oblique illumination 22.

The processor may be configured to determine a height of structure 10 by comparing an integrated intensity generated by the TDI sensor to a calibration curve or a look up table. The calibration curve or the look up table may be determined prior to measurement of an unknown specimen by inspecting and/or measuring structures having known heights. The heights of the structures may be known using another independent measurement technique calibrated with a standard reference material traceable, for example, to NIST or another national testing authority. The structures having known heights may also have characteristics, dimensions, materials, and/or structures similar to the unknown specimen. The processor may have access to a variety of calibration curves or look up tables, and each calibration curve or look up table may be used for specimens having different characteristics, dimensions, materials, and/or structures formed thereon.

The processor may include an image processing device coupled to the imaging system. An image processing device may be a parallel processing system that may be commonly used by the machine vision industry. The image processing device may be configured to generate an image of an illuminated area of specimen 12. The image processing device may also be coupled to a host computer (not shown) that may be configured to control the system and to perform data processing functions. For example, data processing functions may include, but are not limited to, flagging defective structures by comparing a determined height of the structure to a predetermined range of the height of the structure, automatic defect classification, extracting a structure layout on the specimen from the data acquired from the TDI sensor, providing surface and volume information from the data, providing summary files and defect map files such as an industry standard KLA results format (KLARF) wafer map commercially available from KLA-Tencor, determining if the specimen should be reworked or repaired, and determining if a defect is in a critical or non-critical portion of a specimen. An example of a method for determining if a defect is in a critical portion of a specimen is illustrated in PCT Application No. WO 00/36525 by Glasser et al., which is incorporated by reference as if fully set forth herein.

The processor may also be configured to determine and/or alter a parameter of a process tool used to process the specimen using a feedback and/or feedforward control technique. For example, the processor may use feedforward or feedback algorithms to alter a parameter of an instrument coupled to a process tool. The feedforward or feedback algorithms may include algorithms that include variables for, but not limited to, the specific process tool that processed the specimen, the process parameter used to process the specimen, a history of the process tools and/or process steps performed on the specimen, and the maintenance history of the process tool. The algorithms may run in conjunction with advanced process control algorithms that may be included in commercially available software such as Catalyst available from KLA-Tencor. Data for the above variables may include information collected from process tools throughout a fab and may be organized and stored in a fab database using commercially available software such as PMC-Net also available from KLA-Tencor.

As shown in FIG. 1, the imaging system may also include TDI sensor 52, which may also be referred to as a "reference TDI." TDI sensor 52 may be coupled to an optical system (not shown) configured to collect and/or focus light returned from the specimen onto the TDI sensor. In one embodiment, as shown in FIG. 4, optical system 42 may be coupled to both measurement TDI 40 and reference TDI 52. In this manner, optical system 42 may collect and focus light in partially-illuminated field of view 68 onto measurement TDI 40 and may also collect and focus light in fully-illuminated field of view 70 onto reference TDI 52. Coupling a single acquisition lens to both TDI sensors of the system may provide advantages such as increasing the simplicity of the optical system, increasing the convenience of the system, and increasing the speed or throughput of the system. The acquisition lens may be an equivalent lens to the objective lens described above. The acquisition lens may also be configured to have a variable magnification depending on, for example, ranges of height of structures and/or specimens being inspected and/or measured and selected resolving capability. The acquisition lens may include any collection lens or objective lens known in the art.

TDI sensor 52 may be configured to detect full oblique illumination returned from the specimen. For example, TDI sensor 52 may be positioned such that the sensor may form a reference image of an area of the specimen that is wholly within illuminated area 34 of partial oblique illumination 22 on specimen 12. In this manner, a portion of the specimen may be scanned with full oblique illumination, and TDI sensor 52 may form a reference image of the structure under full oblique illumination. The TDI sensor may also be configured to integrate an intensity of the reference image. Therefore, two images of a structure may be integrated in succession as the structure is passed laterally across the fields of view of TDI sensors 40 and 52 (i.e., a measurement image as the object passes across the oblique terminator imaged on the specimen by the imaging system and a reference image obtained in full oblique illumination). Alternatively, the imaging system may include another sensor such as a charge coupled device ("CCD") camera or another camera known in the art in place of TDI sensor 52.

Figure 9:
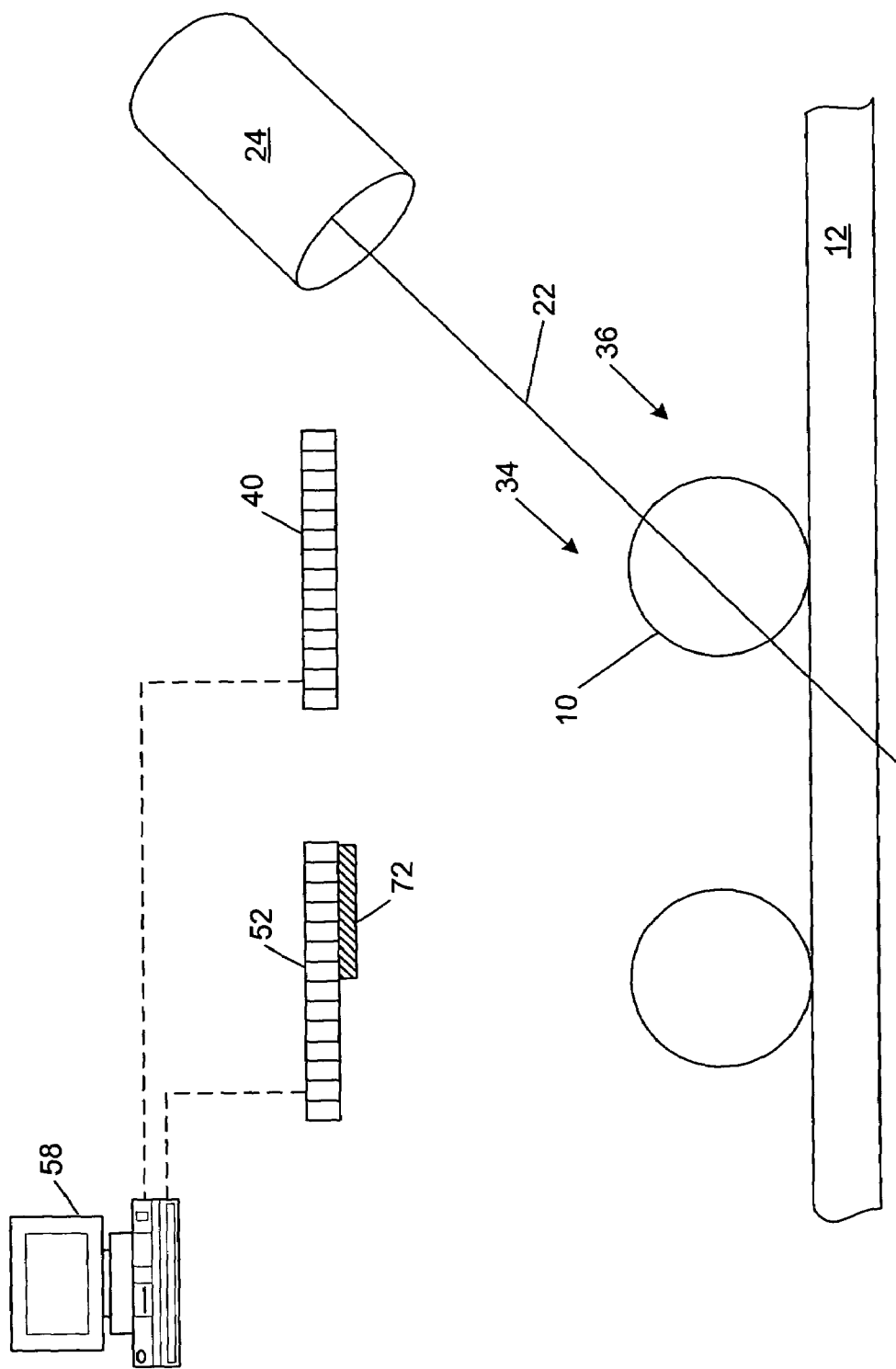
FIG. 9 is a partial schematic cross-sectional view of an embodiment of a system configured to determine a dimension of a structure on a specimen, in which a reference TDI sensor is partially blocked.

As shown in FIG. 9, TDI sensor 52 may be coupled to blocking device 72, which may include, for example, a shutter. In this manner, TDI sensor 52 may be blocked, or otherwise controlled, such that only a percentage of the pixels of the TDI sensor are used to generate the reference image. As such, TDI sensor 52 may perform only a percentage of the total integration across the sensor (i.e., about 15% to about 75% integration, or about 50% integration). In this manner, an image formed by TDI sensor 52 may more closely match an image formed by TDI sensor 40 by reducing the differences between illumination used to form the images. Other methods for reducing the reference image exposure may employ a neutral density filter or an attenuating beam splitter. Such a blocking device, blocking method, or another control method, however, may not be used, and differences between the illumination used to form the images may be reduced using, for example, a model or a calibration curve.

As shown in FIG. 5, as the specimen is scanned in direction x over a period of time, t, bumps 74 having a height greater than bumps 76 will both be fully illuminated by the illumination system because both bumps would be located in illuminated area 34. TDI sensor 52 detects an image of bumps 74 and 76 as the images move across the TDI sensor. Intensity $I_{74}$ and $I_{76}$ of the images of bumps 74 and 76, respectively, are shown to be different in FIG. 5. Such variations in the intensity are generally caused by albedo differences between the bumps, which may cause certain bumps to appear brighter than others. Albedo differences may be generally defined as the fraction of light or other electromagnetic radiation reflected by a surface. In some cases, however, the intensity of different sized bumps may be approximately equal.

Processor 58 may be configured to reduce, or even normalize, albedo differences between structures on the specimen using the reference image. As such, the system may reduce error in height measurements of structures due to differences in surface characteristics of the structures. For example, the processor may be configured to reduce albedo differences by determining the ratio of the integrated intensities of the image and the reference image. The processor may be configured to determine a height of a structure by comparing the ratio of the integrated intensities to a calibration curve or a look up table as described above. Alternatively, the system may not include reference TDI sensor 52 as described above. In such an embodiment, processor 58 may be configured to model the albedo differences between structures on a specimen and to reduce, or even normalize, the albedo differences on the height measurements of the system.

As shown in FIG. 1, the system may also include stage 44. Stage 44 may be configured to support the specimen during scanning of the specimen. The stage may also be configured to move the specimen such that the imaging system may scan the specimen. For example, the stage may move the specimen in direction, x, as shown in FIG. 5, relative to TDI sensors 40 and 52. Alternatively, the stage may be configured to remain stationary while the illumination system and the TDI sensors are moved such that the imaging system may scan the specimen. In addition, a vertical position of the stage may be substantially constant during scanning of the specimen. For example, after the specimen may be brought substantially into focus by altering a vertical position of the stage or a vertical position of the imaging system prior to performing inspection and/or measurement, stage 44 may not be moved in a direction indicated by vector 78, as shown in FIG. 1 during inspection and/or a measurement. Such a system is substantially different than some conventional 3D inspection and metrology systems that are configured to alter a vertical position of a specimen several times to obtain several confocal images of the structure at various vertical positions. In additional embodiments, the stage and/or the illumination system and the TDI sensors may be configured to move such that the imaging system may scan the specimen in other directions. For example, the imaging system may scan the specimen in the x-direction as described above and/or in the y-direction, which is substantially perpendicular to the x-direction.

Figure 10:
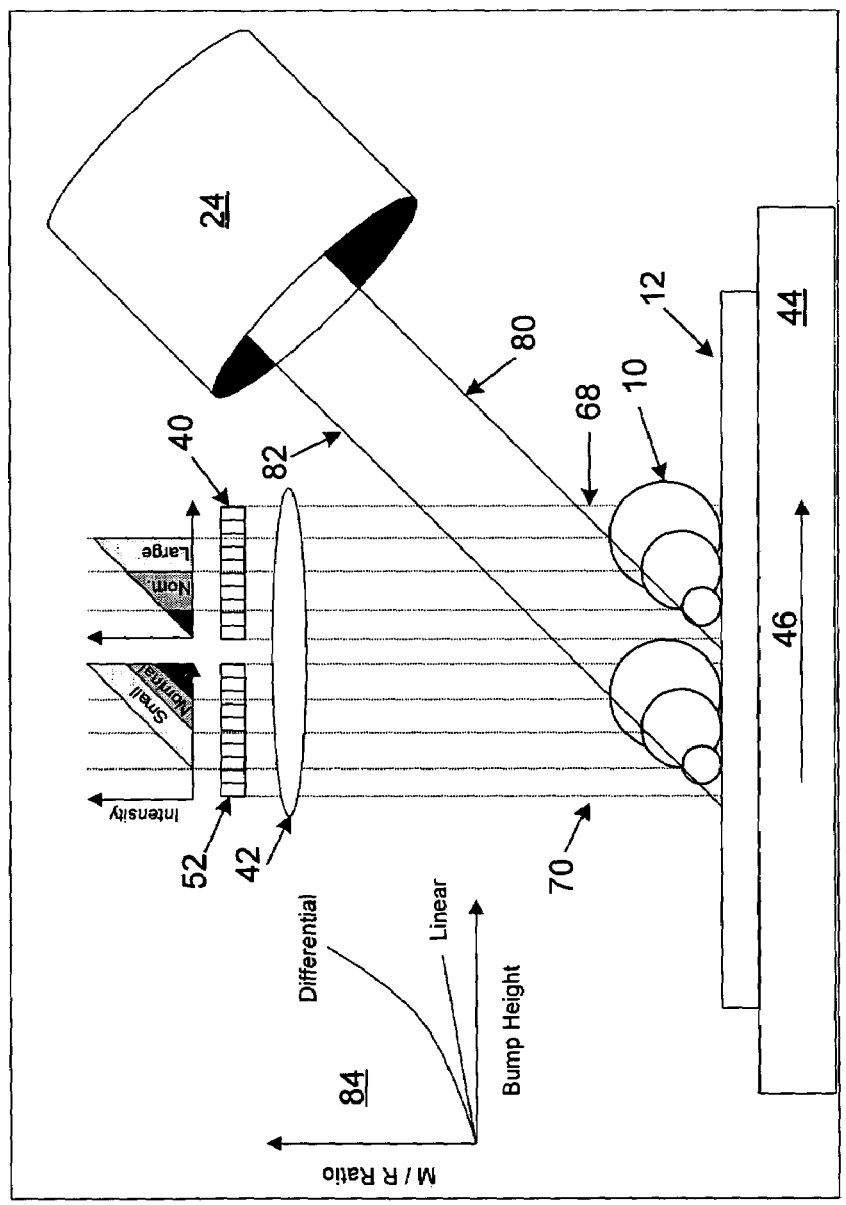
FIGS. 10–11 are partial schematic cross-sectional views of various embodiments of a system configured to determine a dimension of a structure on a specimen, which projects two or more knife edge terminators on the specimen.

FIG. 10 illustrates a partial schematic cross-sectional view of an embodiment of a system configured to determine a dimension of a structure on a specimen by projecting two or more knife edge terminators on the specimen. In this embodiment, illumination system 24 is configured to project knife edge terminators 80 and 82 on the specimen at the same azimuthal angle. Knife edge terminator 82 is inverted with respect to knife edge terminator 80. In addition, measurement TDI 40 is configured to image structure 10 as it passes across knife edge terminator 80, and reference TDI 52 is configured to image structure 10 as it passes across knife edge terminator 82.

This "two knife edge terminators with differential response" configuration adds a second, inverted knife edge that images under the reference TDI, as shown in FIG. 10. This second knife edge terminator has the reverse configuration from the first (i.e., the illumination is below the shadow instead of above it). Because of the inversion of illumination areas and non-illuminated areas, the reference TDI now sees structure intensities that are inversely proportional to their height. The measurement TDI sees structure exposures proportional to their heights. FIG. 10 shows graphs representing the intensities for three bump heights (small, nominal and large) as they integrate across each of the two TDIs. The resulting ratio of the measurement TDI response to the reference TDI response ("M/R response") is the square of the linear response, which can be obtained as described above, as shown in graph 84. The system shown in FIG. 10 may be further configured as described herein.

Figure 11:
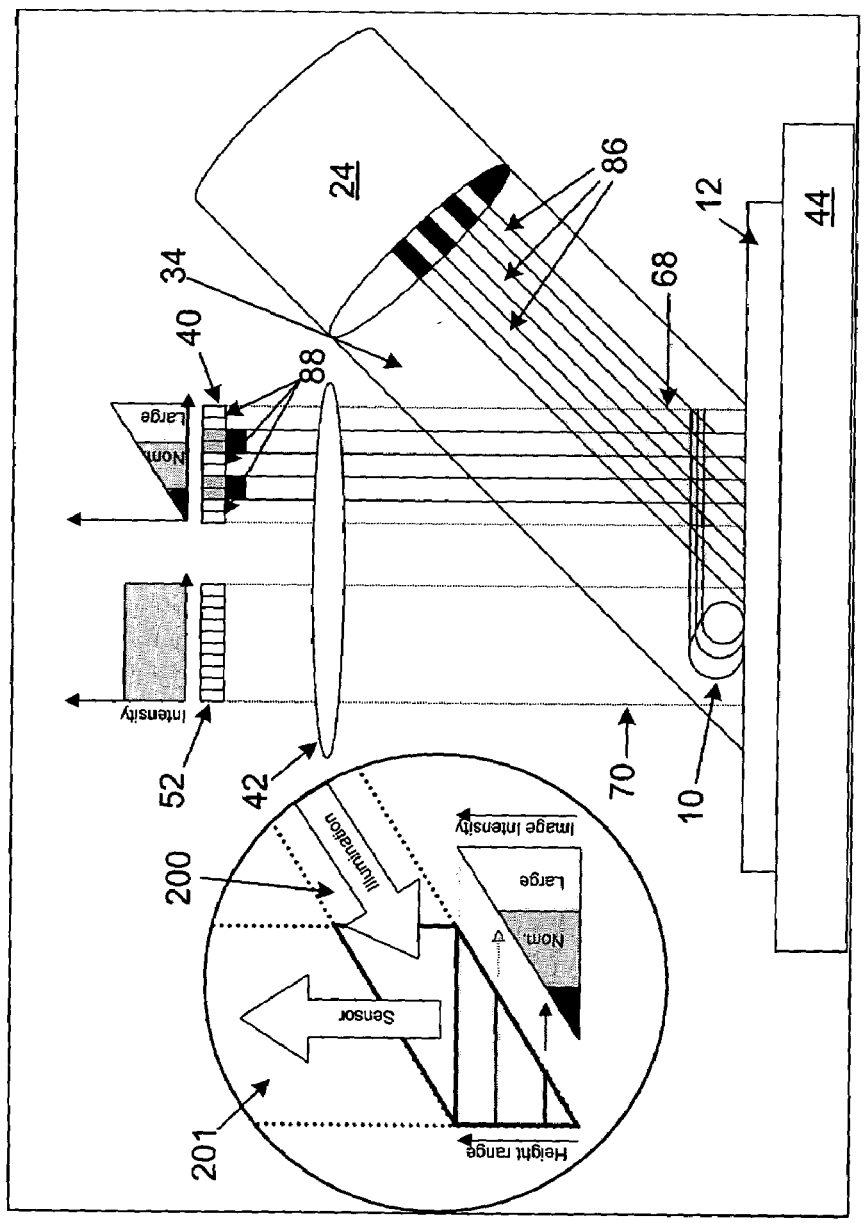

FIG. 11 illustrates a partial schematic cross-sectional view of a different embodiment of a system configured to determine a dimension of a structure on a specimen by projecting two or more knife edge terminators on the specimen. A series of knife edge terminators 86 and matching slits 88 on measurement TDI 40 are arranged so that structures 10 receive an increasing amount of light through a specific height measurement range. In this manner, the measurement TDI sensor may integrate an image of a structure multiple times as it passes across each of the two or more knife edge terminators. Between minimum and maximum height, specimens receive light directly proportional to their heights, across multiple regions. Above this height range, and depending on the relative width and angles of the illuminated region 200 and imaged region 201, a taller structure's image intensity will be inversely proportional to its height or its intensity will remain at constant exposure for a range of heights before becoming inversely proportional to height above that range.

The system illustrated in FIG. 11 uses an array of knife edge terminators on a single oblique illumination system 24 and a matching array of slits on the measurement TDI. This technique boosts the measurement signal-to-noise ratio by applying multiple exposure-based measurements across the measurement TDI instead of just one. The amount of overlap between the illuminated areas and the exposed areas of the measurement TDI changes as a function of a structure's height. For a maximum height (labeled "large" in FIG. 11), the system can be set up to maximize the overlap of illuminated and exposed areas giving the brightest exposure possible. Structures that are shorter will have proportionately less overlap between the illuminated areas and exposed areas and consequently, they will get a darker exposure in the measurement TDI. FIG. 11 shows the incremental exposures for each of the exposed regions of the measurement TDI. These areas show the measurement TDI response for each of the three different bump heights. As described herein, the reference TDI may get a full exposure for each of the structures and may normalize any reflectance differences between structures.

Note that structures taller than the "large" structure in FIG. 11 will receive a decreasing amount of light. The slits and knife edge terminators can be configured such that the measurement range falls in the upper half of the parallelogram that marks the overlap between illumination and exposed sensor. In that configuration, exposure will be inversely proportional to height. Alternatively, the nominal specimen height can be located at the crossover point between the lower and upper halves of the parallelogram thereby giving the maximum exposure at the nominal height and less exposures to height both above and below nominal.

Figure 12:
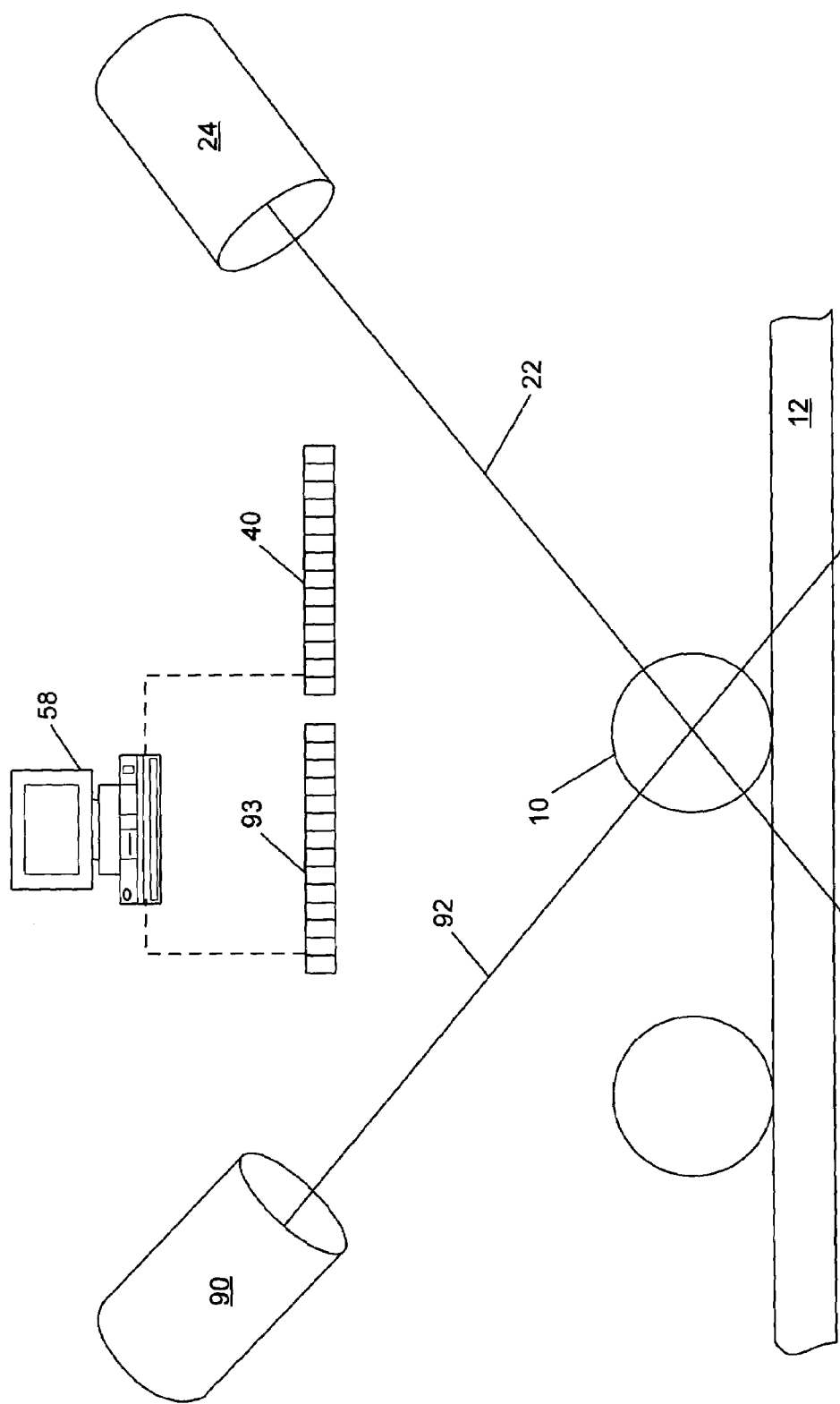
FIG. 12 is a partial schematic cross-sectional view of an embodiment of a system configured to determine a dimension of a structure on a specimen having multiple partial oblique illumination channels.

FIG. 12 illustrates a partial schematic side view of an embodiment of a system configured to determine a dimension of a structure on a specimen having multiple partial oblique illumination channels. For example, the imaging system may include additional illumination system 90. The additional illumination system may be configured to project partial oblique illumination 92 onto specimen 12. Illumination system 24 and additional illumination system 90 may have approximately equal angles of illumination across the field of view. Alternatively, illumination system 24 and additional illumination system 90 may have substantially different angles of illumination across the field of view. In this manner, the two illumination systems may be used to scan specimens having structures with a relatively broad range of heights and/or substantially different types of structures. The additional illumination system, however, may be configured to project partial oblique illumination 92 onto the specimen from a different azimuthal angle than partial oblique illumination 22. The additional illumination system may also be configured to project partial oblique illumination 92 onto the specimen from different azimuthal and/or polar angles than partial oblique illumination 22. For example, as shown in FIG. 12, illumination system 24 and additional illumination system 90 may be configured to project partial oblique illumination 22 and 92, respectively, at substantially opposite azimuthal angles and/or the same or different polar angles. Both of the partial oblique illumination channels, however, may be arranged at any azimuthal angles with respect to each other, any azimuthal angles with respect to the swath, and/or any azimuthal angles with respect to the scanning direction. For example, both of the partial oblique illumination channels may be arranged at an azimuthal angle of about 0° or about 90° with respect to the scanning direction. The additional illumination system may be further configured as described herein.

The system may also include TDI sensor 93, which in this embodiment is configured to form an additional image of the specimen and to integrate the intensity of the additional image. The TDI sensor may be coupled to an acquisition lens (not shown) or another collection or objective lens known in the art as described above. TDI sensor 93 may be configured to form the additional image from collected partial oblique illumination 92 returned from the specimen. In addition, the multiple partial oblique illumination channels may have different wavelengths, different polarizations, or another different characteristic. In this manner, TDI sensors 40 and 93 may be configured to detect light from only one of the partial oblique illumination channels thereby reducing, or even eliminating, effects due to scattering from the multiple channels. The imaging system may also include additional TDI sensors (not shown), of which each may be configured to form a reference image of the structure for one of the two partial oblique illumination channels. The additional TDI sensors may be further configured as described above.

In the embodiment of FIG. 12, the processor may be configured to determine a height of a structure on the specimen from the integrated intensities generated by TDI sensors 40 and 93. Such a system may reduce shadowing of areas between structures thereby increasing the sensitivity of the system to 3D defects formed between structures on the specimen. In addition, such a system may be configured to determine a height based on images formed over substantially an entire surface of the structure. The system shown in FIG. 12 may be further configured as described herein.

Figure 13:
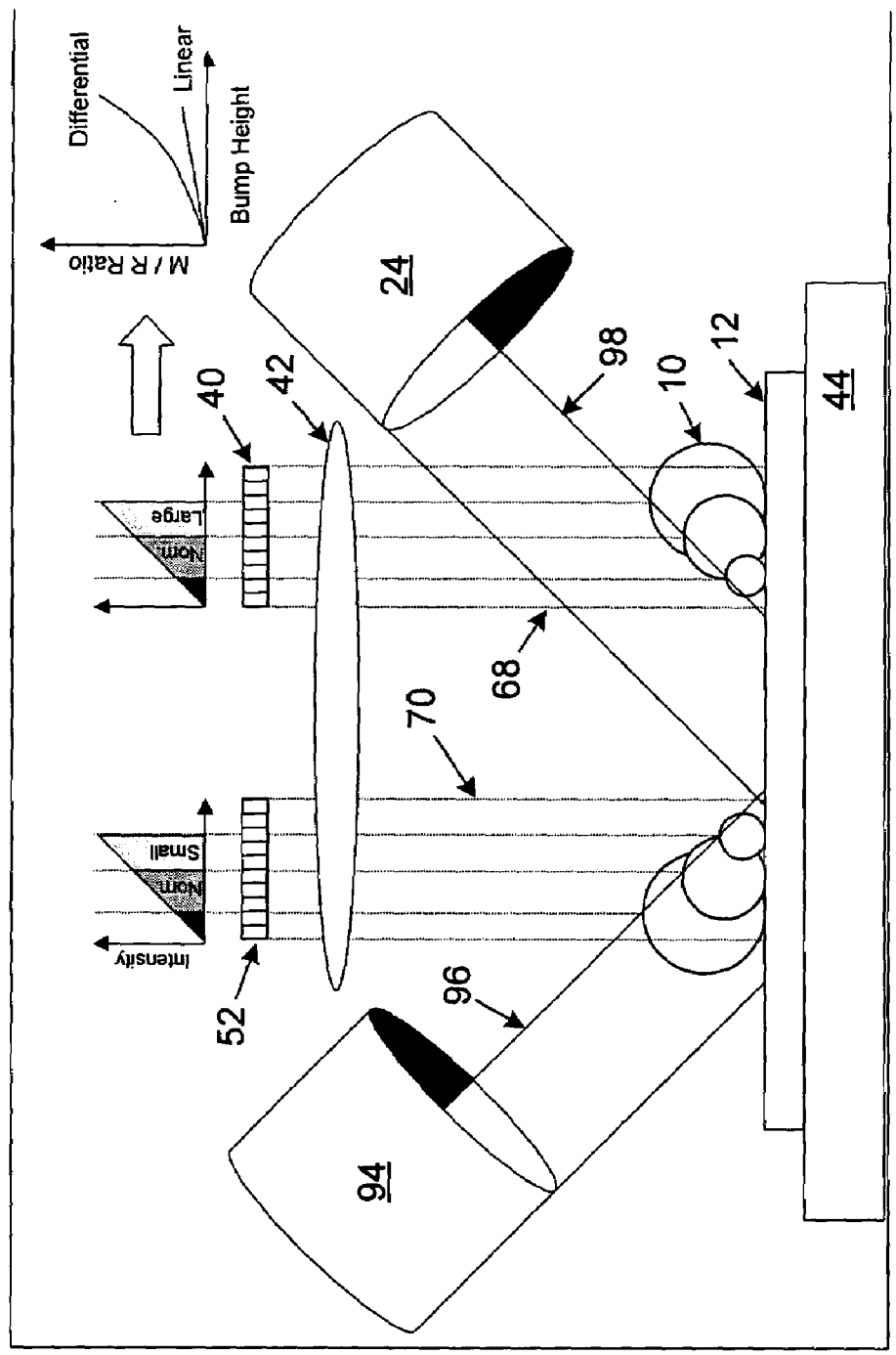
FIGS. 13–14 are partial schematic cross-sectional views of various embodiments of a system configured to project two knife edge terminators on a specimen at different azimuthal angles.

FIG. 13 illustrates one embodiment of a system that is configured to project two opposing knife edge terminators onto a specimen. This illumination configuration provides a differential and squared response. Opposing additional illumination system 94 projects knife edge terminator 96 onto specimen 12. The illumination region is below the non-illumination region blocked off by knife edge terminator 96. Therefore, knife edge terminator 96 is inverted with respect to knife edge terminator 98 projected onto specimen 12 by illumination system 24. In this manner, the system has an inverted knife edge terminator configuration. Measurement TDI 40 images the structure as it passes across knife edge terminator 98, and reference TDI 52 images the structure as it passes across knife edge terminator 96. Reference TDI 52 field of view gets partial illumination in a configuration that is inverted with respect to the other oblique illumination. Therefore, additional illumination system 94 provides a reference TDI exposure that is inversely proportional to structure height. The inverted configuration provides an exposure that is inversely proportional to structure height. The final measurement TDI response to reference TDI response ratio ("M/R response") is the square of the linear response, which can be obtained as described above. The system shown in FIG. 13 may be further configured as described herein.

Figure 14:
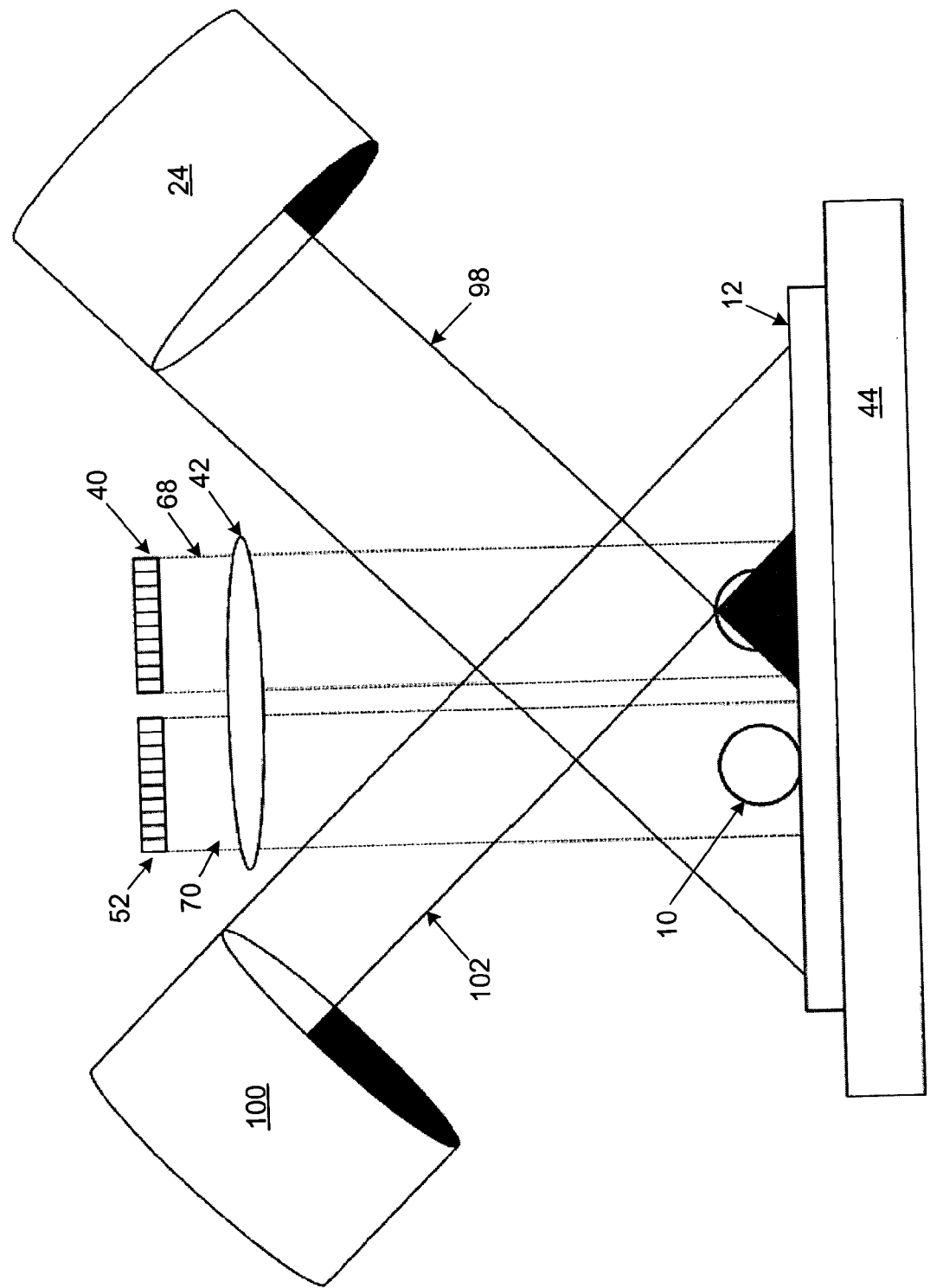

FIG. 14 illustrates a different embodiment of a system that is configured to project two opposing knife edge terminators onto a specimen. This system is configured to project two knife edge terminators onto the specimen with doubled measurement intensity to increase a structure's intensity as imaged by the measurement TDI. As shown in FIG. 14, additional illumination system 100, which may be located opposite illumination system 24, projects knife edge terminator 102 across structures under the measurement TDI. The measurement image gets two exposures that are proportional to the specimen's height. This configuration reduces the height measurement error of the system. For diffusely scattering surfaces, an increased amount of light reaching the measurement TDI results in smaller errors for height below the nominal. For specular reflections, the additional illumination system adds another specular dot, which may be opposite that of illumination system 24, thereby providing more information about the shape of the structure and a second height measurement of the structure. The system shown in FIG. 14 may be further configured as described herein.

Figure 15:
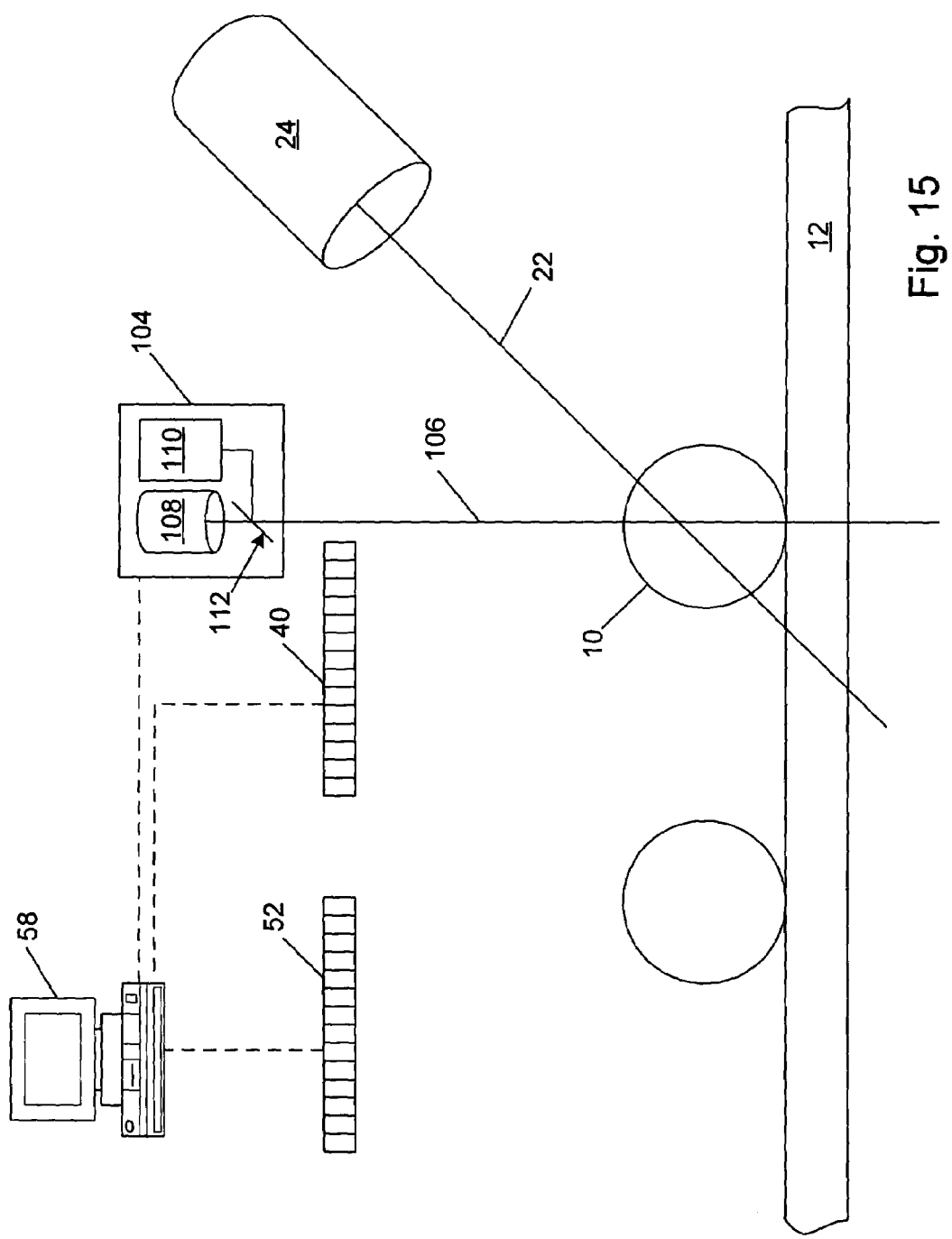
FIG. 15 is a partial schematic cross-sectional view of an embodiment of a system configured to perform multi-dimensional metrology and inspection of a specimen.

FIG. 15 depicts a partial schematic side view of an embodiment of a system configured to perform multi-dimensional metrology and inspection of a specimen. The system may be configured as described herein. In addition, the system includes second imaging system 104 configured to form a bright field image of the specimen by scanning specimen 12 with bright field illumination 106 and detecting the bright field illumination reflected or scattered from the specimen. The second imaging system 104 may also be configured to form a dark field image by detecting partial oblique illumination reflected or scattered from the specimen. Both bright field illumination 106 and oblique illumination 22 may support 2D metrology and inspection of the specimen. For example, second imaging system 104 includes light source 108 configured to project light to the specimen such that the light may be scanned across the specimen. The light source may include any of the light sources as described above. An angle of illumination of second imaging system 104 may be approximately normal to an upper surface of the specimen. In addition, the bright field illumination and partial oblique illumination channels may have different wavelengths, different polarizations, or another different characteristic. In this manner, TDI sensor 40 and sensor 110 of the second imaging system may be configured to detect light from only one of the illumination channels thereby reducing, or even eliminating, effects due to scattering from the multiple channels.

Figure 16:
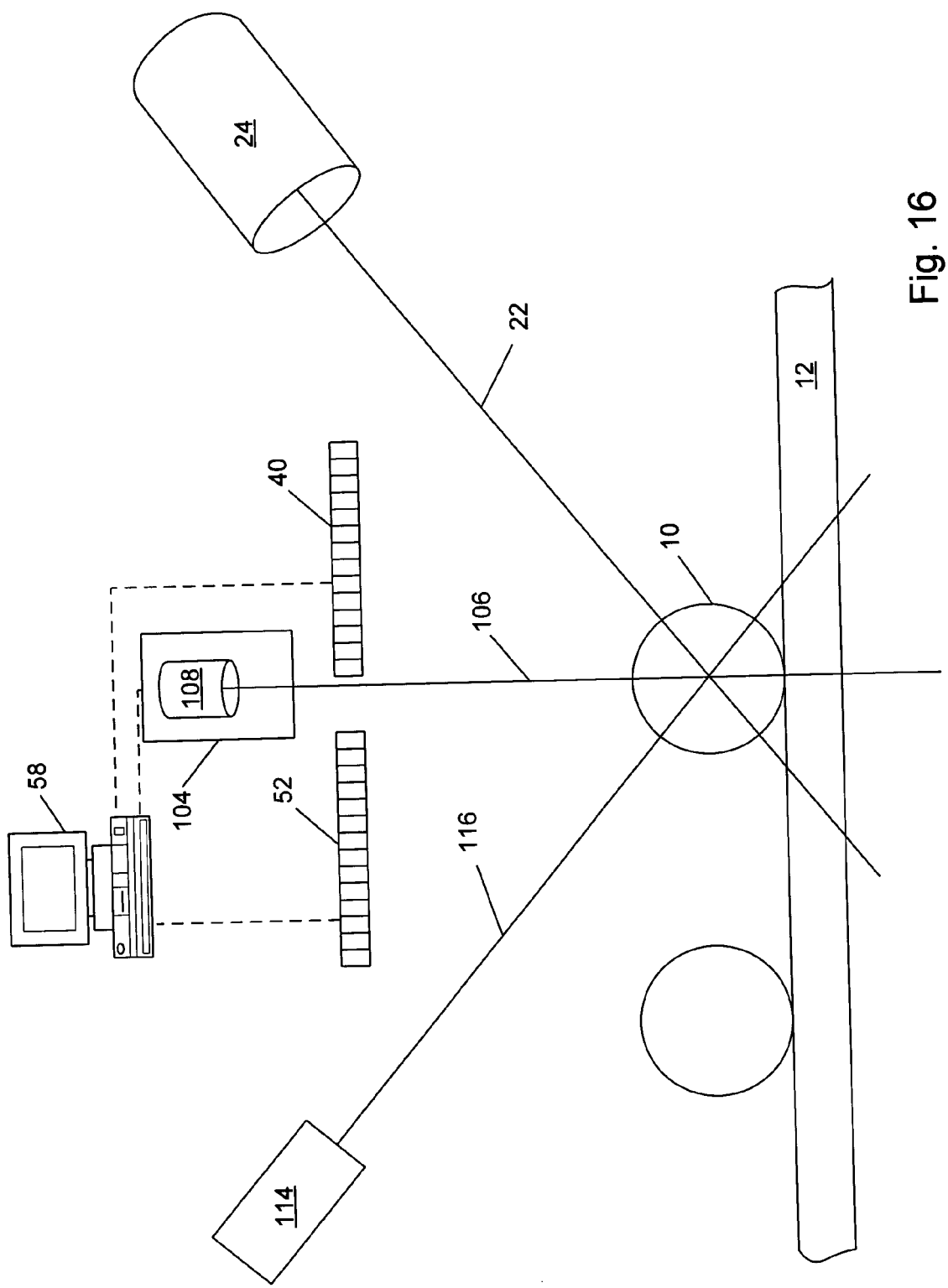
FIG. 16 is a partial schematic cross-sectional view of an embodiment of a sensor that may be included in a system configured to perform multi-dimensional metrology and inspection of a specimen.

Sensor 110 for second imaging system 104 may be configured to detect light specularly reflected from the specimen. In such an embodiment, the sensor may be disposed within second imaging system 104. The specularly reflected light may be directed to the sensor by components of the second imaging system. For example, light returned from the specimen may be directed to sensor 110 by beam splitter 112 or another suitable optical component. Alternatively, the sensor of second imaging system 104 may be configured to detect light scattered from the specimen. For example, as shown in FIG. 16, sensor 114 may be arranged at an oblique angle to the specimen. In this manner, sensor 114 may detect light from the normal illumination channel that is scattered from the specimen. An appropriate sensor 114 for the second imaging system may include, for example, a TDI sensor, a linear CCD camera, or any other appropriate device known in the art. Another appropriate sensor 114 for the second imaging system may include a pair of TDI sensors, which may be configured as described herein.

Second imaging system 104 may include other optical elements including, but not limited to, objective lenses (not shown) coupled to the light source and the sensor. The partial oblique imaging system may also include other optical elements such as objective lenses coupled to various components thereof. In addition, an objective lens may be coupled to one or more of the light sources and/or the sensors. For example, in a system such as that shown in FIG. 16, one objective lens may be coupled to illumination system 24, another objective lens may be coupled to sensors 40 and 52 and optionally light source 108, and a third objective lens may be coupled to sensor 114. Coupling a single objective lens to multiple components of the system may provide advantages such as increasing the simplicity of the optical system, increasing the convenience of the system, and increasing the speed or throughput of the system. The second imaging system may be further configured as known in the art. For example, the second imaging system may be configured as the two-dimensional defect detection portion of a commercially available inspection system such as the ABI-2000, which is commercially available from KLA-Tencor.

The height measurement methods and systems described herein may be used for both specular and diffuse reflections of the partial oblique illumination. For example, in another embodiment, sensor 114 may be configured to detect light 116 from the partial oblique illumination channel that is specularly reflected from the specimen, as shown in FIG. 16. An appropriate sensor for such an embodiment may include a pair of TDI sensors, which may be configured as described herein. In this manner, light from the partial oblique illumination channel that is scattered from the specimen may be detected by TDI sensors 40 and 52, and light 116 from the partial oblique illumination channel that is specularly reflected from the specimen may be detected by sensor 114. In such a system, an objective lens (not shown) may preferably be coupled to sensor 114 such that the knife edge projected onto the specimen may be focused onto the sensor. Light from the partial oblique illumination channel that is scattered and specularly reflected from the specimen may be detected sequentially or simultaneously. In addition, only scattered or specularly reflected light from the partial oblique illumination channel may be detected. This embodiment may or may not be configured for 2D metrology and inspection of the specimen using bright field and/or dark field illumination of the specimen as described above. For example, second imaging system 104 may be omitted from the embodiment illustrated in FIG. 16.

Figure 17:
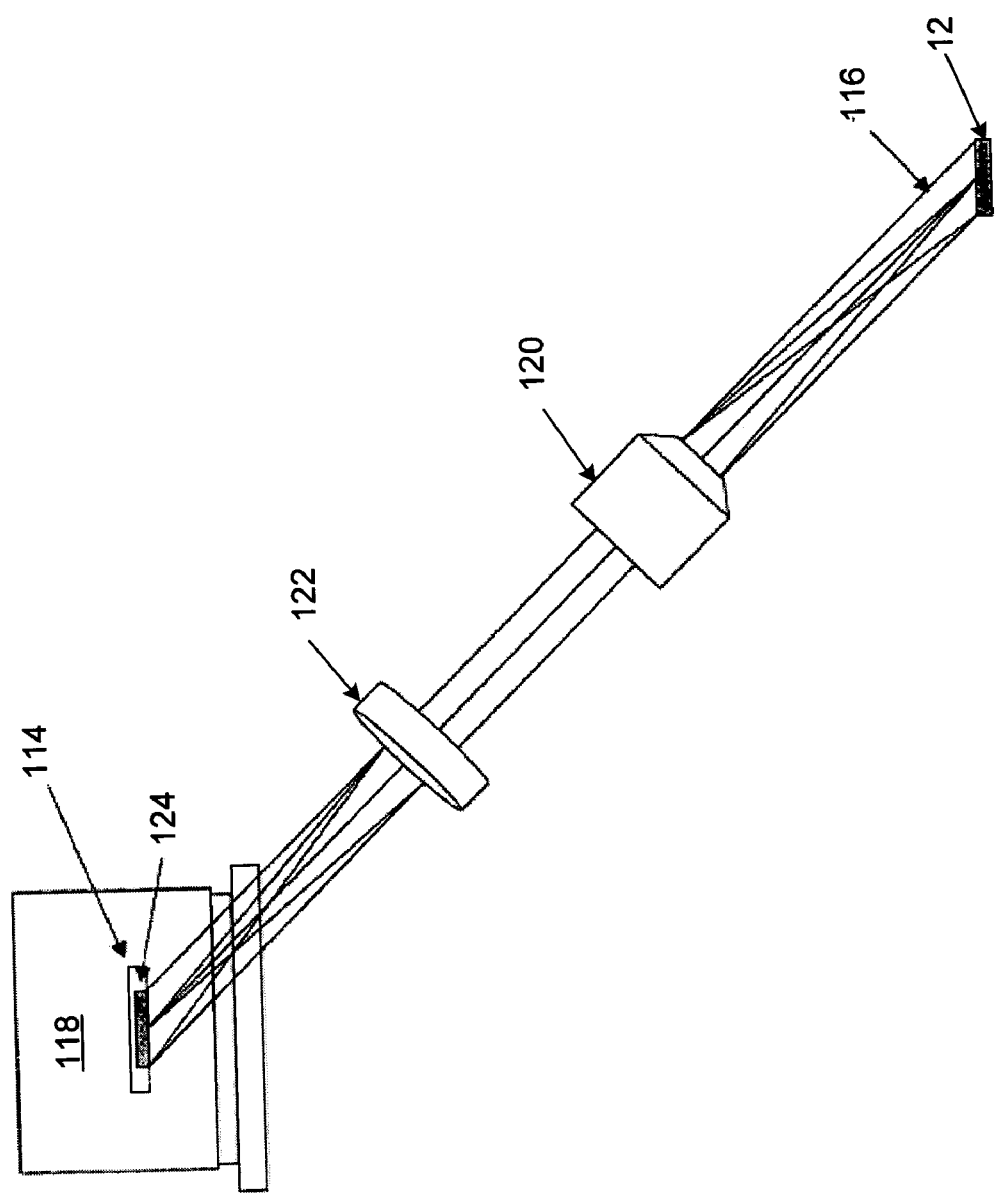
FIG. 17 is a partial schematic cross-sectional view of an embodiment of a sensor and imaging system configuration that may be particularly useful in forming an image of a specimen at an oblique angle.
Figure 18:
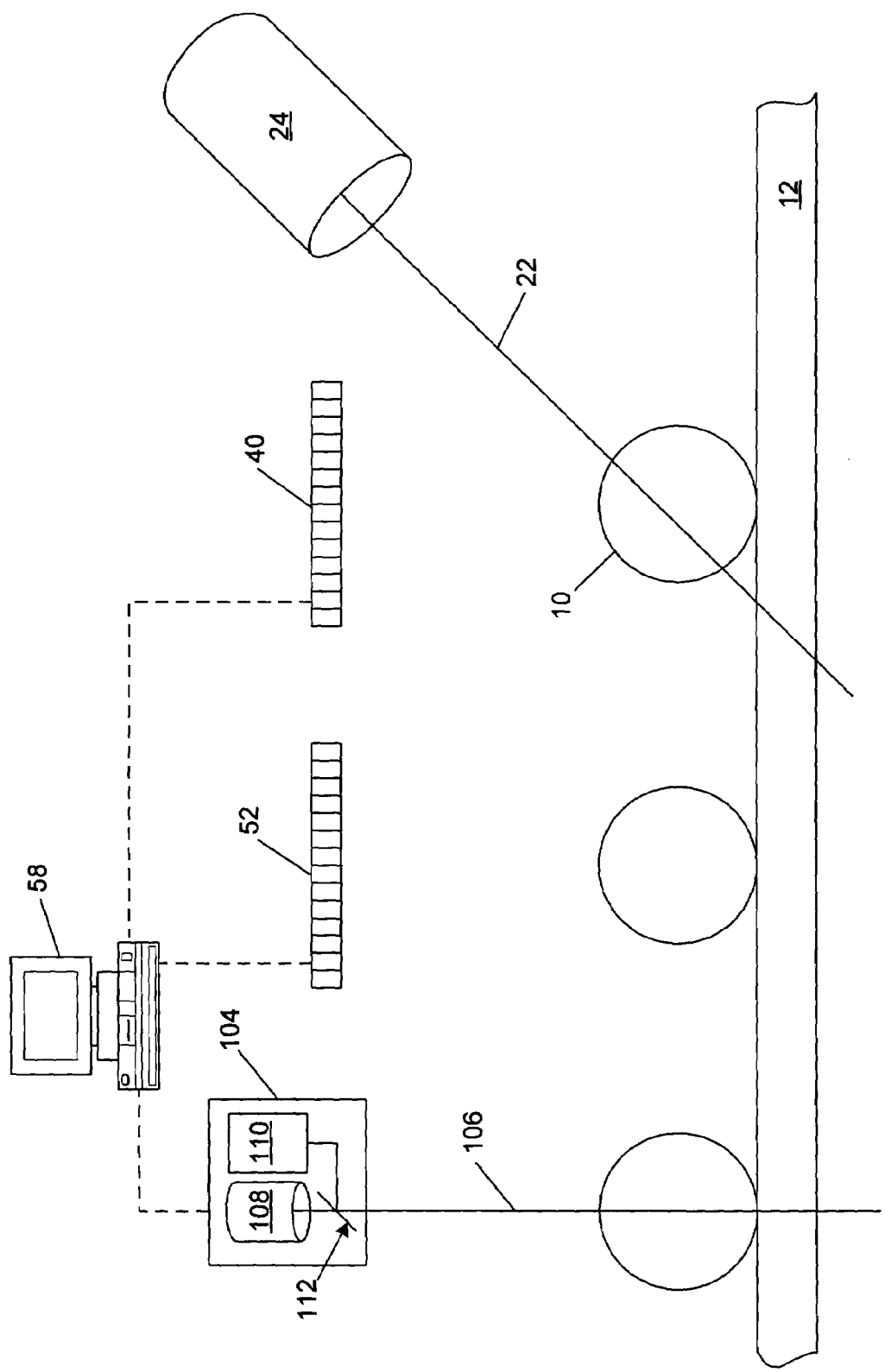
FIGS. 18–19 are partial schematic cross-sectional views of additional embodiments of a system configured to perform multi-dimensional metrology and inspection of a specimen.

FIG. 17 illustrates another embodiment of sensor 114 that may be included in the system of FIG. 16. The embodiment of sensor 114 illustrated in FIG. 17 may be particularly useful for detecting light from the partial oblique illumination channel that is specularly reflected from specimen 12. As shown in FIG. 17, sensor 114 may be included in camera 118. Camera 118 may include any other components known in the art. In some embodiments, more than one lens may be coupled to sensor 114. For example, as shown in FIG. 17, two lenses 120 and 122 may be coupled to the sensor. The two lenses may include objective lens 120 and tube lens 122 or any other lenses known in the art such as relay lenses or magnification lenses.

As further shown in FIG. 17, sensor 114 may have a focal plane that is arranged at an angle with respect to the focal plane at the specimen. For example, the sensor may be "tipped" with respect to the lenses. In this manner, the focal plane of the sensor may be commonly referred to as a "tipped focal plane." Such a focal plane may advantageously provide image 124 of the specimen that is more proportionate to the specimen across the field of view, in a direction that the specimen is scanned, than a sensor that does not have such a tipped focal plane. In such embodiments, the uniformity of the image may also be increased if the sensor has a relatively high depth of focus.

Whether scattered or specularly reflected partial oblique illumination is used for 3D metrology and inspection of a specimen may vary depending on, for example, characteristics of the specimen. For example, in some embodiments, a relatively small amount of partial oblique light may be scattered by the specimen, but a relatively large amount of partial oblique light may be specularly reflected from the specimen. Therefore, using the partial oblique light specularly reflected from the specimen, instead of partial oblique light scattered by the specimen, may increase the sensitivity of the system to the height of a structure on the specimen. In one example, a specimen may include structures such as reflowed bumps formed thereon. The reflowed bumps may have a fairly uniform, shiny, and spherical surface. Therefore, such a structure may specularly reflect a relatively large amount of partial oblique light. For example, the reflowed bumps may specularly reflect the partial oblique illumination to a relatively small, sharp area on sensor 114. Therefore, light of the partial oblique illumination channel that is specularly reflected from the specimen may be used to detect a height of the reflowed bumps thereby increasing the sensitivity of the height measurements. However, such a structure may scatter relatively little of the partial oblique illumination. For example, the scattered light may be weaker in intensity, and may be more spread out than the specularly reflected light. Therefore, light of partial oblique illumination channel that is scattered from the specimen may be used to increase the accuracy of the height measurements. In other embodiments, a specimen may scatter significantly more of the partial oblique illumination than that which is specularly reflected from the specimen. In this embodiment, the light scattered from the specimen, not the light specularly reflected from the specimen, may be used to determine a height of a structure on the specimen.

Processor 58 may be also be coupled to second imaging system 104, oblique sensor 114, and/or any other imaging system included in the system. For example, processor 58 may be coupled to at least a sensor of second imaging system 104, oblique sensor 114, and/or any other imaging system included in the system. Processor 58 may be configured to detect defects on the specimen from a bright field or dark field image formed by second imaging system 104, oblique sensor 114, and/or any other imaging system included in the system. The defects may include two-dimensional defects on the specimen. Two-dimensional defects may include, but are not limited to, missing structures, improperly located structures, bridged structures, large-lateral dimension structures, and small-lateral dimension structures. For a specimen such as a bumped wafer, 2D defects may include, but are not limited to, missing bumps, improperly located bumps, bridged bumps, large-diameter bumps, and small-diameter bumps. In addition, processor 58 may be configured to determine a lateral dimension such as a width, a length, or a diameter of structure 10 from the bright field image or dark field image. Furthermore, as described above, processor 58 may be configured to determine a height of structure 10 from an integrated intensity generated by TDI sensor 40 or TDI sensors 40 and 52 or an off-axis arrangement similar to sensor 114.

Such an embodiment of the system, therefore, may be configured to perform 2D and 3D inspection and metrology. Furthermore, because the imaging system and second imaging system 104 and/or any other imaging system included in the system may be configured to scan an area on the specimen substantially simultaneously, the system may be configured to perform 2D and 3D inspection and metrology substantially simultaneously. Alternatively, the imaging system and second imaging system 104 and/or any other imaging system included in the system may simply be configured to scan the specimen in the same pass. For example, in an alternative embodiment illustrated in FIG. 18, second imaging system 104 and/or any other imaging system included in the system may be laterally spaced from the imaging system such that the imaging systems may be configured to scan the specimen in series. The system shown in FIG. 18 may be further configured as described herein.

Figure 19:
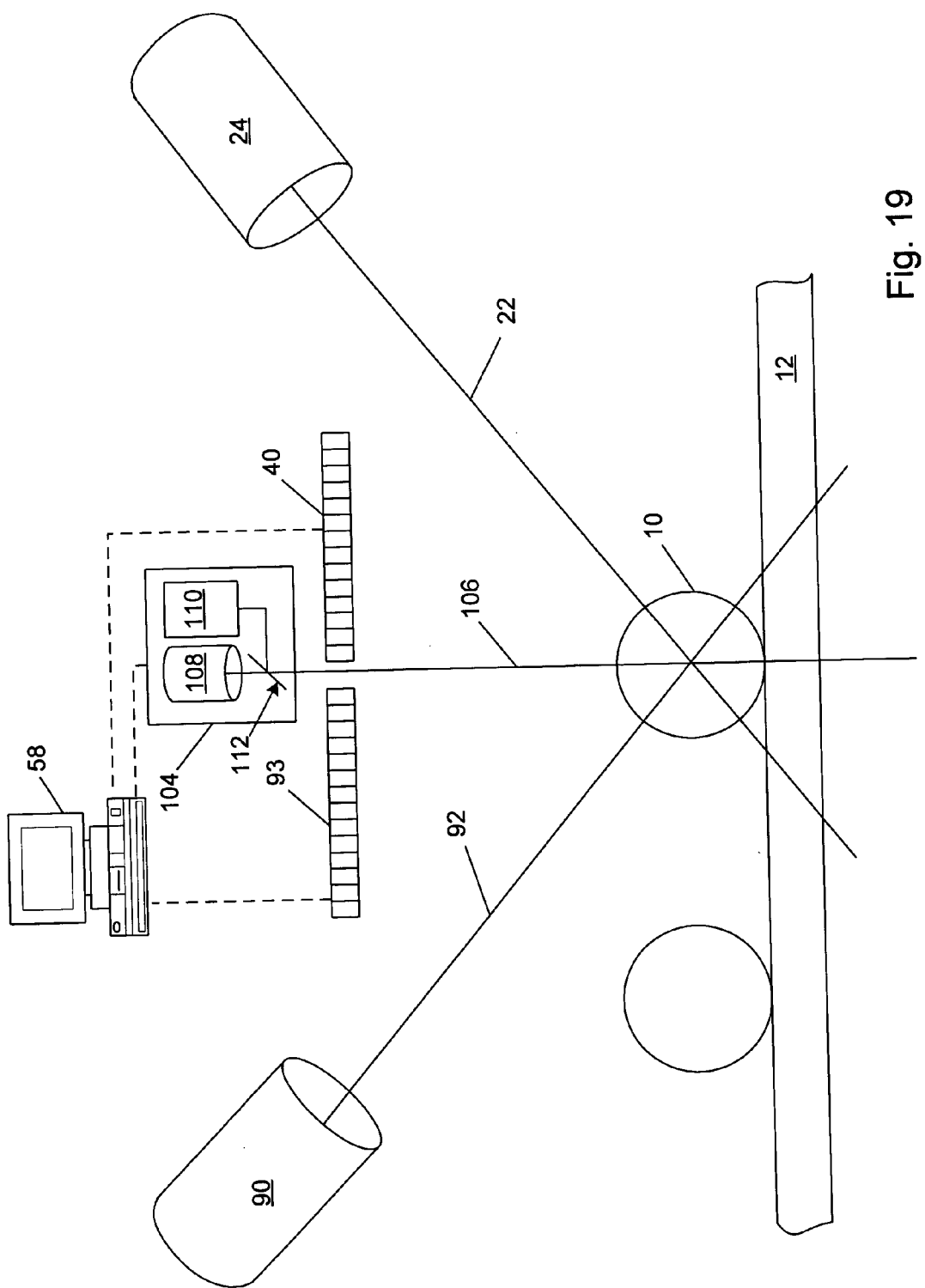

FIG. 19 illustrates an additional embodiment of a system configured to perform multi-dimensional metrology and inspection of a specimen. The system may be configured to determine a dimension of a structure on a specimen using multiple partial oblique illumination 22 and 92 as described herein. The system may also include multiple TDI sensors 40 and 93 configured to form an image of specimen 12 from each partial oblique illumination channel as described herein. In addition, the multiple partial oblique illumination channels may have different wavelengths, different polarizations, or another different characteristic. The system may include other components and may be further configured as described herein. In addition, the system may include second imaging system 104 configured to form a bright field image of the specimen by scanning the specimen with bright field illumination 106 for 2D inspection and metrology. Bright field illumination 106 may have a different wavelength, different polarization, or another different characteristic than both partial oblique illumination 22 and 92. Such an embodiment may be configured to perform 2D and 3D inspection and metrology substantially simultaneously or simply within the same pass as described herein.

Each of the embodiments of a system described above may also include a stage, as shown in FIG. 1. The stage may be configured to support the specimen during scanning of the specimen as described above. The stage may also be configured to move the specimen such that the imaging system may scan the specimen. Alternatively, the stage may be configured to remain stationary while the illumination system and the TDI sensors are moved such that the imaging system may scan the specimen. In addition, a vertical position of the stage may be substantially constant during scanning of the specimen by these systems. For example, after the specimen is brought substantially into focus by altering a vertical position of the stage or the optics of the imaging system prior to performing inspection and/or measurement, the stage may not be moved substantially in a direction indicated by vector 78, as shown in FIG. 1 in order to perform inspection and/or a measurement. As described above, such a system is substantially different than some conventional 2D and 3D inspection and metrology systems that are configured to alter a vertical position of a specimen several times to obtain several confocal images of the structure at various vertical positions.

Various systems as described herein may also be used to perform other methods, measurement techniques, and/or inspection techniques. For example, various systems as described herein may be used as an autofocus mechanism. Various systems as described herein may also be used as an autofocus mechanism in a conventional inspection tool having a bright field or dark field channel. For example, the system may be configured to monitor topography across a specimen, such as a wafer, as a measurement or inspection is being performed on the specimen. In this manner, the system may be used to maintain substantially correct focus of the specimen during the measurement or inspection. For example, the system may provide a feedback mechanism to a stage of the system such that a vertical position of the stage may be altered or to an optical system or measurement head of the system such that a vertical position of the measurement head may be altered during measurement or inspection. The specimen may have an upper surface that includes elevational disparities or that may be relatively flat. In this manner, the system may be also used to detect defects on a specimen having a relatively flat surface or to perform a stress measurement on a specimen.

Figure 20:
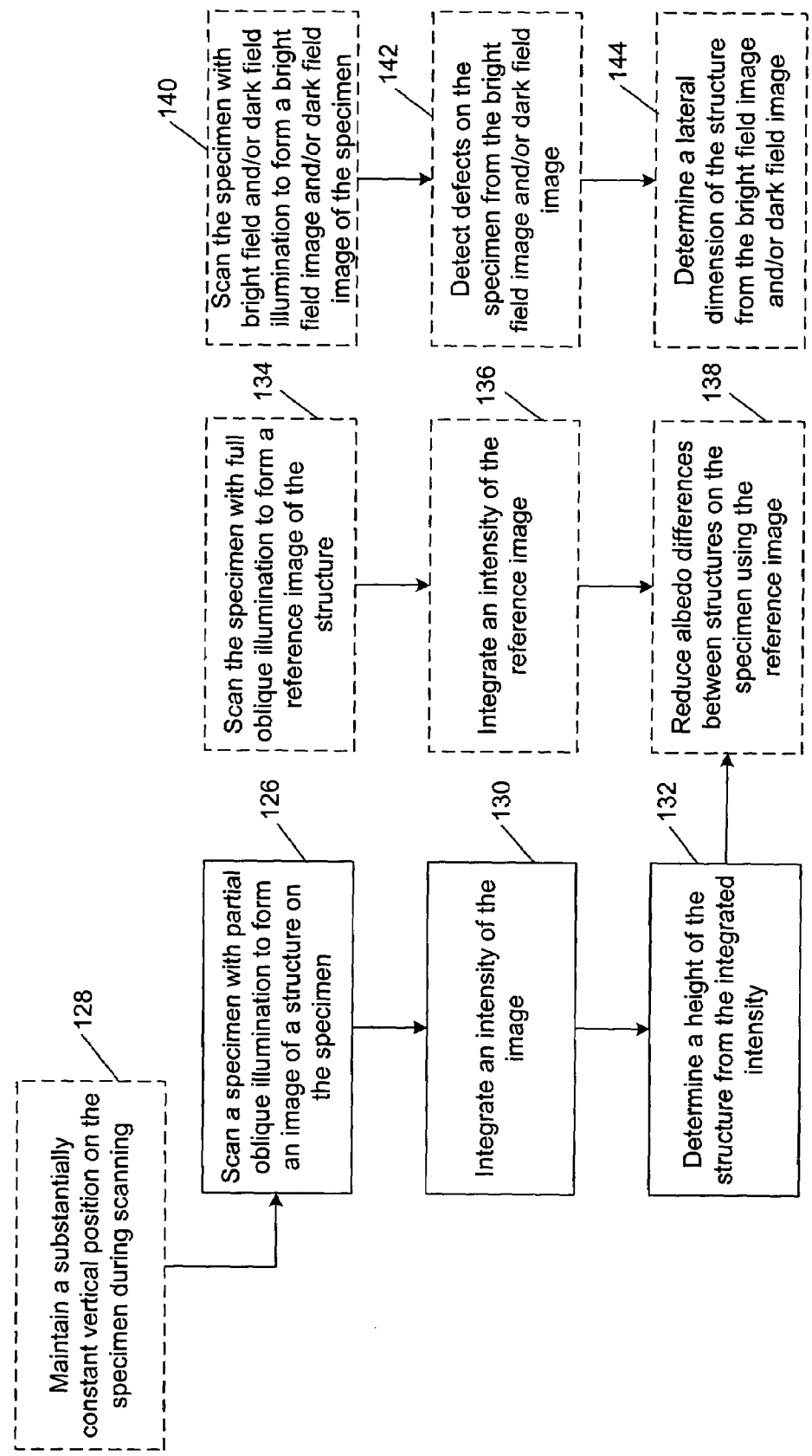
FIG. 20 is a flow chart illustrating various embodiments of methods for determining a dimension of a structure on a specimen.

FIG. 20 is a flow chart illustrating various methods for determining a dimension of a structure on a specimen. The structure and the specimen may include any of the structures and specimens, respectively, as described herein. The method includes scanning the specimen with partial oblique illumination to form an image of the structure, as shown in step 126. Scanning the specimen may include imaging the structure as it passes across an obliquely-projected knife edge terminator on the specimen according to one embodiment. In some embodiments, scanning may include projecting two or more knife edge terminators on the specimen at the same azimuthal angle as described above. In one such embodiment, scanning may also include forming different images of the structure as it passes across each of the two or more knife edge terminators. In one embodiment, the image may be a smeared image of the structure, which may be formed as described above. In a different embodiment, the image may be magnified in a direction in which scanning is performed. The magnified image may also be formed as described above.

In an embodiment, an angle of the partial oblique illumination may be substantially constant during scanning of the specimen. In an additional embodiment, the method may include maintaining a substantially constant vertical position of the specimen during scanning of the specimen, as shown in step 128. The method also includes integrating an intensity of the image, as shown in step 130. In addition, the method includes determining a height of the structure from the integrated intensity of the image, as shown in step 132. The integrated intensity may be approximately proportional or approximately inversely proportional to the height of the structure as described herein. In some embodiments, the method may include determining a height of a surface of the specimen from the integrated intensity.

In an embodiment, the method may also include scanning the specimen with full oblique illumination to form a reference image of the structure, as shown in step 134. Such a method may also include integrating an intensity of the reference image, as shown in step 136. In an embodiment, the method may include determining a height of the structure from the integrated intensities of the image and the reference image as described herein. In a further embodiment, the method may include reducing, or even eliminating, albedo differences between structures on the specimen using the reference image, as shown in step 138.

In an additional embodiment, the method may include scanning the specimen with additional partial oblique illumination at an azimuthal angle different than the partial oblique illumination to form an additional image of the structure. Such an embodiment may also include integrating an intensity of the additional image. The method may further include determining a height of the structure from the integrated intensity of the additional image. The additional image may also be approximately proportional to the height of the structure.

In addition, the method may include scanning the specimen with bright field illumination to form a bright field image of the specimen, as shown in step 140. In an embodiment, scanning the specimen with partial oblique illumination and bright field illumination may be performed substantially simultaneously. In an additional embodiment, the method may include maintaining a substantially constant vertical position of the specimen during scanning of the specimen with partial oblique illumination and bright field illumination. The method may include determining a height of the structure from the integrated intensity as described above. Furthermore, the method may include detecting defects on the specimen from the bright field image, as shown in step 142. The method may further include determining a lateral dimension of the structure from the bright field image, as shown in step 144.

Further modifications and alternative embodiments of various aspects of the invention may be apparent to those skilled in the art in view of this description. For example, systems and methods for multi-dimensional metrology and/or inspection of a specimen are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to determine a dimension of a structure on a specimen, comprising:
   a partial oblique illumination system configured to project a knife edge terminator on the specimen;
   an imaging system configured to image the structure as the structure passes across the knife edge terminator and to integrate an intensity of the images of the structure; and
   a processor coupled to the imaging system, wherein the processor is configured to determine a height of the structure from the integrated intensity.

2. The system of claim 1, wherein the processor is further configured to determine a height of a surface of the specimen from the integrated intensity.

3. The system of claim 1, wherein the integrated intensity is proportional or inversely proportional to the height of the structure.

4. The system of claim 1, wherein the partial oblique illumination system comprises an objective lens configured to image the knife edge terminator on the specimen, and wherein the objective lens has a numerical aperture selected such that an angle at which the knife edge terminator is projected onto the specimen is substantially constant.

5. The system of claim 1, wherein the imaging system is further configured to image the structure as the structure passes across an additional knife edge terminator projected onto the specimen at an azimuthal or polar angle different than an azimuthal or polar angle at which the knife edge terminator is projected on the specimen.

6. The system of claim 5, wherein the imaging system comprises a measurement time delay integration sensor configured to image the structure as it passes across the knife edge terminator and a reference time delay integration sensor configured to image the structure as it passes across the additional knife edge terminator.

7. The system of claim 5, wherein the additional knife edge terminator is inverted with respect to the knife edge terminator.

8. The system of claim 1, wherein the imaging system is further configured to image the structure as the structure passes across an additional knife edge terminator projected onto the specimen at an azimuthal angle opposite that at which the knife edge terminator is projected on the specimen.

9. The system of claim 8, wherein the additional knife edge terminator is inverted with respect to the knife edge terminator.

10. The system of claim 8, wherein the additional knife edge terminator is non-inverted with respect to the knife edge terminator.

11. The system of claim 1, wherein the imaging system comprises a time delay integration sensor configured to image the structure and to integrate the intensity.

12. The system of claim 1, wherein the imaging system comprises a time delay integration sensor configured to image the structure and to integrate the intensity, and wherein the sensor is operated at a speed greater than a speed of a stage on which the specimen is supported during imaging such that the images are smeared.

13. The system of claim 1, wherein the imaging system comprises a time delay integration sensor configured to image the structure and to integrate the intensity, and wherein the sensor has an asymmetric pixel size such that pixels of the sensor have a dimension in a scan direction that is smaller than a dimension of the pixels in a direction opposite to the scan direction.

14. The system of claim 1, wherein the imaging system comprises a time delay integration sensor configured to image the structure and to integrate the intensity, and wherein anamorphic optics are coupled to the sensor such that the image is magnified in a scan direction.

15. The system of claim 1, wherein the imaging system is further configured to form a reference image of the structure in full oblique illumination and to integrate an intensity of the reference image, and wherein the processor is further configured to reduce albedo differences between the structure and additional structures on the specimen using the reference image.

16. The system of claim 1, wherein the imaging system is further configured to form a reference image of the structure in full oblique illumination and to integrate an intensity of the reference image, and wherein the processor is further configured to determine the height of the structure from the integrated intensities of the image and the reference image.

17. The system of claim 1, wherein the partial oblique illumination system is further configured to project two or more knife edge terminators on the specimen at the same azimuthal angle.

18. The system of claim 17, wherein the imaging system comprises a measurement time delay integration sensor configured to image the structure as it passes across a first of the two or more knife edge terminators and a reference time delay integration sensor configured to image the structure as it passes across a second of the two or more knife edge terminators.

19. The system of claim 17, wherein the imaging system comprises a measurement time delay integration sensor configured to form multiple exposures of the structure as it passes across each of the two or more knife edge terminators.

20. The system of claim 17, wherein the imaging system comprises a measurement time delay integration sensor having slits that match the two or more knife edge terminators.

21. The system of claim 1, further comprising a stage configured to support the specimen during imaging, wherein a vertical position of the stage is substantially constant during imaging.

22. The system of claim 1, wherein the structure comprises a bump, a ball, or a surface, and wherein the specimen comprises a wafer, a sawn wafer, a die, or an integrated circuit package.

23. The system of claim 1, wherein the structure comprises a three-dimensional defect.

24. A method for determining a dimension of a structure on a specimen, comprising:
scanning the specimen with partial oblique illumination such that the structure passes across an oblique plane separating an illuminated region and a non-illuminated region in the partial oblique illumination to form an image of the structure;
integrating an intensity of the image; and
determining a height of the structure from the integrated intensity.

25. The method of claim 24, further comprising determining a height of a surface of the specimen from the integrated intensity.

26. The method of claim 24, wherein the integrated intensity is proportional or inversely proportional to the height of the structure.

27. The method of claim 24, wherein the oblique plane comprises an obliquely-projected knife edge terminator separating the illuminated and non-illuminated regions.

28. The method of claim 24, wherein an angle of the partial oblique illumination is substantially constant during said scanning.

29. The method of claim 24, further comprising scanning the specimen with additional partial oblique illumination at an azimuthal angle different than the partial oblique illumination to form an additional image of the structure and integrating an intensity of the additional image.

30. The method of claim 24, wherein said scanning comprises projecting two or more knife edge terminators on the specimen at the same azimuthal angle.

31. The method of claim 30, wherein said scanning further comprises forming multiple exposures of the structure as it passes across each of the two or more knife edge terminators.

32. The method of claim 24, wherein the image comprises a smeared image of the structure.

33. The method of claim 24, wherein the image is magnified in a direction in which said scanning is performed.

34. The method of claim 24, further comprising scanning the specimen with full oblique illumination to form a reference image of the structure, integrating an intensity of the reference image, and reducing albedo differences between the structure and additional structures on the specimen using the reference image.

35. The method of claim 24, further comprising scanning the specimen with full oblique illumination to form a reference image of the structure and integrating an intensity of the reference image, wherein said determining comprises determining the height of the structure from the integrated intensities of the image and the reference image.

36. The method of claim 24, further comprising maintaining a substantially constant vertical position of the specimen during said scanning.

37. The method of claim 24, wherein the structure comprises a bump, a ball, or a surface of the specimen, and wherein the specimen comprises a wafer, a sawn wafer, a die, or an integrated circuit package.

38. The method of claim 24, wherein the structure comprises a three-dimensional defect.

39. A system configured to determine a dimension of a structure on a specimen, comprising:
a first imaging system configured to form an image of the structure by scanning the specimen with partial oblique illumination such that the structure passes across an oblique plane separating an illuminated region and a non-illuminated region in the partial oblique illumination;
a second imaging system configured to form a bright field image of the specimen by scanning the specimen with bright field illumination; and
a processor coupled to the first and second imaging systems, wherein the processor or the first imaging system is configured to integrate an intensity of the image, and wherein the processor is further configured to determine a height of the structure from the integrated intensity, to detect defects on the specimen from the bright field image, and to determine a lateral dimension of the structure from the bright field image.

40. The system of claim 39, wherein the first and second imaging systems are further configured to scan the specimen in the same pass.

41. A method for determining a dimension of a structure on a specimen, comprising:
- scanning the specimen with partial oblique illumination such that the structure passes across an oblique plane separating an illuminated region and a non-illuminated region in the partial oblique illumination to form an image of the structure;
- integrating an intensity of the image;
- scanning the specimen with bright field illumination to form a bright field image of the specimen;
- detecting defects on the specimen from the image or the bright field image; and
- determining a height of the structure from the integrated intensity and a lateral dimension of the structure from the bright field image.

42. The method of claim 41, wherein said scanning the specimen with partial oblique illumination and said scanning the specimen with bright field illumination are performed substantially simultaneously.

* * * * *